(12) United States Patent
Ionescu-Zanetti et al.

(10) Patent No.: US 10,240,186 B2
(45) Date of Patent: Mar. 26, 2019

(54) DEVICES, SYSTEMS, AND METHODS FOR MAGNETIC SEPARATION

(75) Inventors: Cristian Ionescu-Zanetti, Berkeley, CA (US); Joshua Tanner Nevill, El Cerrito, CA (US); Michael Schwartz, Oakland, CA (US); Carolyn G. Conant, San Francisco, CA (US); Roger Rudoff, Cupertino, CA (US)

(73) Assignee: FLUXION BIOSCIENCES, INC., South San Francisco, CA (US)

( * ) Notice: Subject to any disclaimer, the term of this patent is extended or adjusted under 35 U.S.C. 154(b) by 790 days.

(21) Appl. No.: 13/183,271

(22) Filed: Jul. 14, 2011

(65) Prior Publication Data

US 2013/0017538 A1   Jan. 17, 2013

(51) Int. Cl.
| | | |
|---|---|---|
| *G01N 33/543* | (2006.01) |
| *C12Q 1/6806* | (2018.01) |
| *B03C 1/28* | (2006.01) |
| *B01L 3/00* | (2006.01) |
| *B01L 7/00* | (2006.01) |

(52) U.S. Cl.
CPC ...... *C12Q 1/6806* (2013.01); *B01L 3/502761* (2013.01); *B03C 1/288* (2013.01); *G01N 33/54326* (2013.01); *B01L 7/52* (2013.01); *B01L 2200/0652* (2013.01); *B01L 2300/0816* (2013.01); *B01L 2300/0864* (2013.01); *B01L 2300/0867* (2013.01); *B01L 2300/0883* (2013.01); *B01L 2400/043* (2013.01); *B03C 2201/18* (2013.01); *B03C 2201/26* (2013.01)

(58) Field of Classification Search
None
See application file for complete search history.

(56) References Cited

U.S. PATENT DOCUMENTS

| | | |
|---|---|---|
| 3,970,518 A | 7/1976 | Giaever |
| 4,157,323 A | 6/1979 | Yen et al. |
| 4,219,411 A | 8/1980 | Yen et al. |
| 4,710,472 A | 12/1987 | Saur et al. |
| 5,053,344 A | 10/1991 | Zborowski et al. |
| 5,409,813 A | 4/1995 | Schwartz |
| 5,508,164 A | 4/1996 | Kausch et al. |

(Continued)

FOREIGN PATENT DOCUMENTS

| | | |
|---|---|---|
| EP | 2191895 B1 | 6/2010 |
| JP | 2004097886 | 4/2004 |

(Continued)

OTHER PUBLICATIONS

Ahn, Chong H. et al., "A fully integrated micromachined magnetic particle separator", Journal of Microelecromechanical Systems 5, No. 3, 1996, pp. 151.

(Continued)

*Primary Examiner* — Robert T. Crow
(74) *Attorney, Agent, or Firm* — Dorsey & Whitney LLP

(57) ABSTRACT

Methods, microfluidic devices, and instruments for magnetic separation of particles from a fluid are described. Examples include microfluidic devices having a removable portion. Examples include microfluidic devices having one or more regions of reduced fluid velocity. Examples further including instruments having pneumatic interfaces. Examples further includes instruments having controllable magnets, imaging components, or combinations thereof.

24 Claims, 15 Drawing Sheets

(56) References Cited

U.S. PATENT DOCUMENTS

| | | | |
|---|---|---|---|
| 5,602,042 A * | 2/1997 | Farber | 436/526 |
| 5,763,203 A | 6/1998 | Ugelstad et al. | |
| 5,795,470 A | 8/1998 | Wang et al. | |
| 5,837,200 A | 11/1998 | Diessel et al. | |
| 5,972,721 A | 10/1999 | Bruno et al. | |
| 6,187,270 B1 | 2/2001 | Schmitt et al. | |
| 6,432,630 B1 | 8/2002 | Blankenstein | |
| 7,138,269 B2 | 11/2006 | Blankenstein | |
| 7,141,415 B2 | 11/2006 | Wirix-speetjens | |
| 2002/0177238 A1* | 11/2002 | Karp et al. | 436/180 |
| 2004/0072278 A1* | 4/2004 | Chou et al. | 435/29 |
| 2004/0260204 A1* | 12/2004 | Boecker et al. | 600/584 |
| 2006/0269385 A1 | 11/2006 | Zobel et al. | |
| 2006/0286549 A1* | 12/2006 | Sohn et al. | 435/5 |
| 2008/0160634 A1* | 7/2008 | Su et al. | 436/501 |
| 2008/0302732 A1 | 12/2008 | Soh et al. | |
| 2009/0053799 A1 | 2/2009 | Chang-yen et al. | |
| 2009/0117004 A1* | 5/2009 | Fritchie et al. | 422/63 |
| 2009/0220932 A1 | 9/2009 | Ingber et al. | |
| 2009/0220979 A1* | 9/2009 | Davis et al. | 435/6 |
| 2009/0264298 A1* | 10/2009 | Lim et al. | 506/1 |
| 2009/0297327 A1* | 12/2009 | Zobel et al. | 414/806 |
| 2010/0252436 A1 | 10/2010 | Park et al. | |
| 2011/0117577 A1 | 5/2011 | Reboud et al. | |

FOREIGN PATENT DOCUMENTS

| | | | |
|---|---|---|---|
| JP | 2005028201 | 2/2005 | |
| WO | 2009008925 A2 | 1/2009 | |
| WO | 2009026566 A1 | 2/2009 | |
| WO | 2009076560 A2 | 6/2009 | |
| WO | WO 2010117458 A1 * | 10/2010 | B03C 1/28 |

OTHER PUBLICATIONS

Azevedo, R. et al., "Morphological study of *Saccharomyces cerevisiae* cells treated with magnetic fluid", Magnetics, IEEE Transactions on 39, No. 5, Sep. 2003, pp. 1660-2662.

Bor Fuh, C. , "Magnetic split-flow thin fractionation: new technique for separation of magnetically susceptible particles", Journal of Chromatography A 813, No. 2, Jul. 17, 1998, pp. 313-324.

Chalmers, J. et al., "Flow-through, immunomagnetic cell separation", Biotechnology Progress 14, No. 1, Feb. 6, 1998, pp. 141-148.

Cho, Brenda S. et al., "Passively driven integrated microfluidic system for separation of motile sperm", Analytical Chemistry 75, No. 7, Apr. 2003, pp. 1671-1675.

Deng, T. et al., "Fabrication of magnetic microfiltration systems using soft lithography", Applied Physics Letters 80, No. 3, 2009, pp. 461-463.

Fiedler, S. et al., "Dielectrophoretic sorting of particles and cells in a microsystem", Analytical Chemistry 70, No. 9, 1998, pp. 1909-1915.

Franzreb, Matthias et al., "Protein purification using magnetic absorbent particles", Applied Microbilolgy and Biotechnology 70, No. 5, Feb. 23, 2006, pp. 505-516.

Fu, A. et al., "A microfabricated fluorescence-activated cell sorter", Nature Biotechnology 17, No. 11, 1999, pp. 1109-1111.

Gleghorn, J. et al., "Capture of circulating tumor cells from whole blood of prostate cancer patients using geometrically enhanced differential immunocature (GEDI) and a prostate-specific antibody", Lab on a Chip 10, No. 1, Jan. 1, 2010, pp. 27.

Handgretinger, R. et al., "Isolation and transplantation of autologous peripheral CD34+ progenitor cells highly purified by magnetic-activated cell sorting", Bone Marrow Transplant, May 1998, pp. 987-993.

Hartig, R. et al., "Continuous sorting of magnetizable particles by means of specific deviation", Review of Scientific Instruments, vol. 66, Issue 5, May 1995, pp. 3289-3295.

Hirschbein, B. et al., "Magnetic separations in chemistry and biochemistry", Chemtech 12, 1982, pp. 172-179.

Huang, L. et al., "Continuous particle separaton through deterministic lateral displacement", Science 304, No. 5673, 2004, pp. 987-990.

Hunt, T. et al., "Addressable micropost array for the dielectrophoretic manipulation of particles in fluid", Applied Physics Letters 85, No. 26, 2004, pp. 6421.

Lee, H. et al., "Manipulation of biological cells using a microelectromagnet matrix", Applied Physics Letters 85, No. 6, 2004, pp. 1063.

Lu, Hang et al., "A microfabricated device for subcellular organelle sorting", Analytical Chenistry 76, No. 19, Oct. 2004, pp. 5705-5712.

Melville, D. et al., "Direct magnetic separation of red cells from whole blood", Nature 255, 1975, pp. 706.

Nagrath, S. et al., "Isolation of rare circulating tumour cells in cancer patients by microchip technology", Nature 450, No. 7173, Dec. 20, 2007, pp. 1235-1239.

Pamme, N. , "Magnetism and microfluidics", Lab on a Chip 6, No. 1, Jan. 1, 2006, pp. 24.

Safarik, I. et al., "Use of magnetic techniques for the isolation of cells", Journal of Chromatography B: Biomedical Sciences and Applications, vol. 722, 1999, pp. 33-53.

Smistrup, K. et al., "Magnetic separation in microfluidic systems using microfabricated electromagnets—experiments and simulations", Journal of Magnetism and Magnetic Materials 293, No. 1, 2005, pp. 597-604.

Takayasu, M. et al., "Continuous magnetic separation of blood components from whole blood", Applied Superconductivity, IEEE Transactions on, vol. 10, No. 1, Mar. 2000, pp. 927-930.

Takayasu, M. et al., "HGMS studies of blood cell behavior in plasma", Magnetics, IEEE Transactions on, vol. 18, No. 6, Nov. 1982, pp. 1520-1522.

Tibbe, A. et al., "Magnetic field design for selecting and aligning immunomagnetic labeled cells", Cytometry 47, No. 3, Feb. 19, 2002, pp. 163-172.

Wang, Mark et al., "Microfluidic sorting of mammalian cells by optical force switching", Nature Biotechnology 23, No. 1, Dec. 19, 2004, pp. 83-87.

Whitesides, G. et al., "Magnetic separations in biotechnology", Trends in Biotechnology, vol. 1, No. 5, 1983, pp. 144-148.

Xia, N. et al., "Combined microfluidic-micromagnetic separation of living cells in continuous flow", Biomedical Microdevices 8, No. 4, Dec. 1, 2006, pp. 299-308.

Xu, Y. et al., "Aptamer-based microfluidic device for enrichment, sorting, and detection of multiple cancer cells", Analytical Chemistry 81, No. 17, Sep. 1, 2009, pp. 7436-7422.

Yamada, M. et al., "Pinched flow fractionation: Continuous size separation of particles uitlizing a laminar flow profile in a pinched microchannel", Analytical Chemistry 76, No. 18, 2004, pp. 5465-5471.

Yang, L. et al., "Optimization of an enrichment process for circulating tumer cells from the blood of head and neck cancer patients through depletion of normal cells", Biotechnolgy and Bioengineering 102, No. 2, Feb. 1, 2009, pp. 521-534.

Zheng, S. et al., "3D microfilter device for viable circulating tumor cell (CTC) enrichment from blood", Biomedical Microdevices, 13, Dec. 27, 2010, pp. 203-213.

PCT International Search Report for PCT/US12/29770, dated Oct. 16, 2012.

Written Opinion for PCT/US2012/29770, dated Oct. 16, 2012.

Supplementary Partial EP Search Report issued for EP Application No. 12811159.8 dated Feb. 25, 2015.

* cited by examiner

100

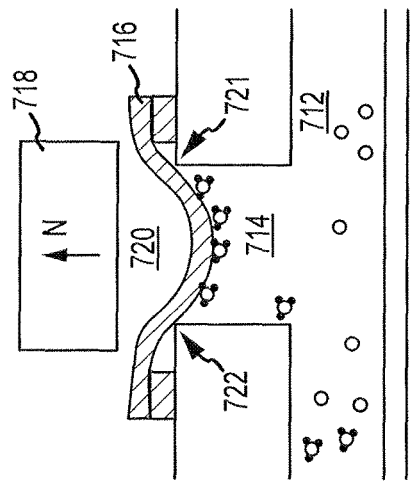
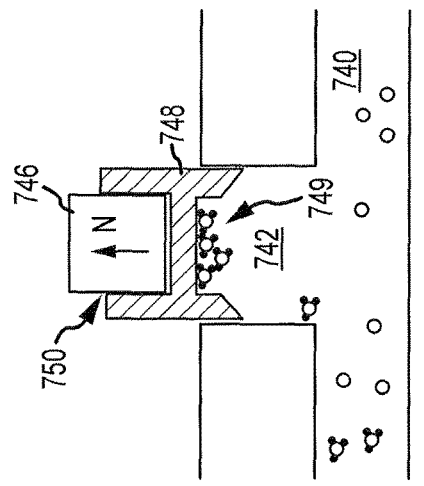
FIGURE 7A
FIGURE 7B
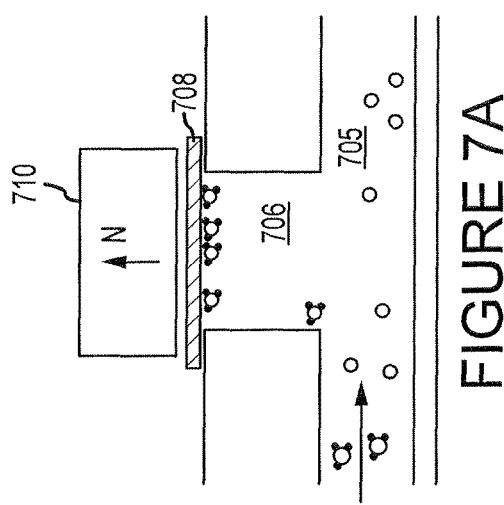
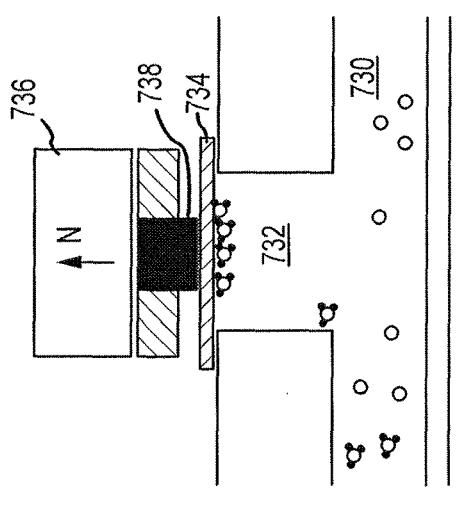
FIGURE 7C
FIGURE 7D

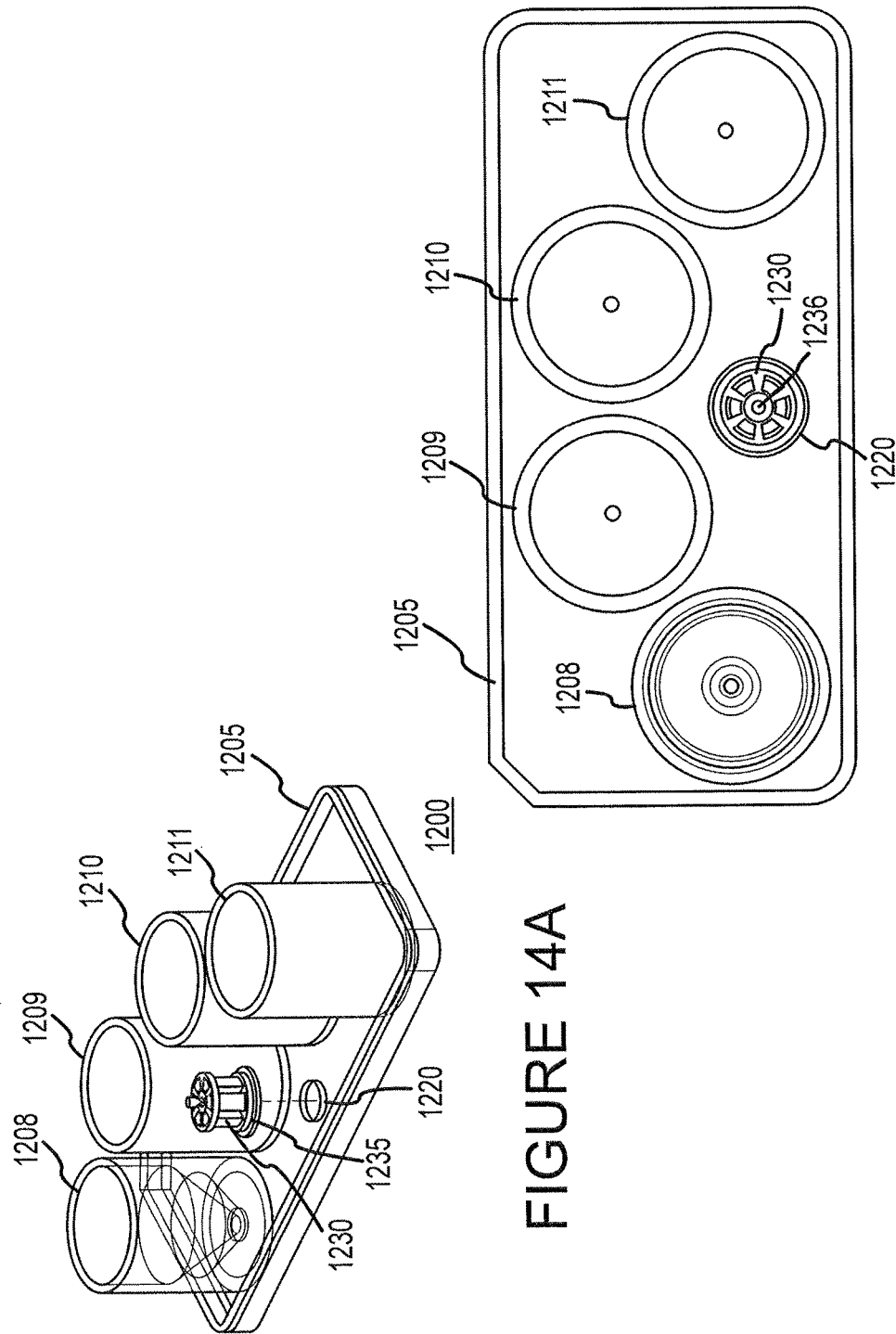

DEVICES, SYSTEMS, AND METHODS FOR MAGNETIC SEPARATION

STATEMENT REGARDING RESEARCH & DEVELOPMENT

Funds used to support some of the studies disclosed herein were provided by grant number 1R43CA141741-0 awarded by the National Institutes of Health from the National Institute for General Medical Sciences. The Government may have certain rights in the invention.

TECHNICAL FIELD

Embodiments of the invention relate generally to the separation of particles having magnetic labels from a fluid. Some described examples include microfluidic devices for magnetic separation.

BACKGROUND

The separation of particles from a fluid may have applications in both the clinical diagnostic and the basic research fields. For a number of applications, separation is performed by applying differential forces to the positive fraction (e.g. cells of interest) and the negative fraction (e.g. background cells). Devices have been described where differences in physical properties have been used to separate specific cells or molecules from solutions of mixed population. These physical properties have included size, motility, electric charge, electric dipole moment, optical qualities, and magnetic susceptibility. Another approach has been to separate cells based on binding of specific surface markers. For example, surfaces of microfluidic channels have been patterned with a variety of antigen capture molecules; a subset of the cell population then interacts with the surface and gets immobilized by binding the surface antigen.

Another approach taken has been to selectively bind beads of a paramagnetic material to the cells of interest, typically via a surface marker present at the cell membrane. The positive fraction is then separated using a magnetic field gradient by either placing a magnet close to the cell suspension or microfluidic channel, or by using an external magnet in order to magnetize structures that have be incorporated in the microscale device thereby amplifying the field gradient in an adjacent region of space. Alternately, the negative fraction can be actively separated, leaving the positive fraction. Various macroscale and microscale devices have been presented in order to separate magnetically labeled species.

BRIEF DESCRIPTION OF THE DRAWINGS

FIGS. 7A-D are schematic illustrations of cross-sections of portions of microfluidic devices arranged in accordance with embodiments of the present invention.

FIGS. 14A and 14B are schematic illustrations of a cartridge and a magnet arranged in accordance with an embodiment of the present invention

DETAILED DESCRIPTION

Figure 1:
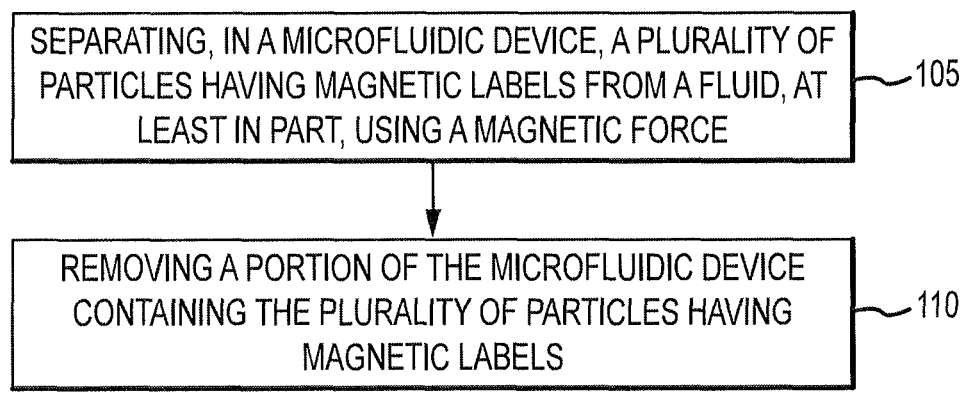
FIG. 1 is a flowchart illustrating a method in accordance with an embodiment of the present invention.

A number of devices and methods have been previously used for the separation of cells or other biological materials of interest from a heterogeneous mixture, as mentioned above. Both macroscopic and micro-scale devices have been envisioned, and a number of particle properties used to enable separation of a positive fraction of cells from a larger population. A variety of cell properties have been used to separate populations, including: fluorescence, cell binding to a substrate, magnetic properties, cell binding to magnetic beads/magnetic forces, inertial properties coupled with acoustic waves, optical and electrical properties of the cells. Previously presented systems may still fall short for a number of applications, especially where the positive fraction represents a very small percentage (<1%) of the total population. The previously presented approaches referenced may have a number of drawbacks which are described below. Embodiments of the present invention may address one or more of these drawbacks, however, the list of drawbacks are provided by way of explanation, and are not intended to limit the scope of the attached claims. Not all of the embodiments of the present invention address all of the below-listed drawbacks, and there may be embodiments of the present invention that do not address any of the below-listed drawbacks.

One drawback of existing systems may be low capture efficiency. During separation, cells may be lost during transfer steps, along a flow path, or eluted downstream along with the negative fraction of the sample.

Another drawback of existing systems may be relatively low purity or concentration of the separated fraction. For a number of analysis techniques, a highly concentrated sample of the positive fraction cells may be required at a high level of purity. This is challenging particularly for samples where the positive fraction represents a very small percentage of the overall sample, such as below 1/1000 or below 1/10E6 cells. To the extent existing separation systems do not completely separate a positive and negative fraction of a sample, a positive fraction of low purity may not be suitable for later analysis techniques.

Another drawback of existing systems may be the inability to recover the positive fraction for downstream analysis. Systems that separate cells by binding the positive fraction to the flow channel walls, for example, cannot remove the bound cells easily for downstream analysis. Either cell lysis or harsh elution steps are required in existing systems if cell recovery is desired. This decreases purity, reduces availability of viable positive fraction cells, decreases the final density of cells in the recovered samples, and increases the complexity of device operation.

Another drawback of existing systems may be an inability to recover viable cells. For example, in systems such as sorting flow cytometers, high flow velocities are required, whereby shear forces significantly impact the viability of separated cells. That is, once a separated cell has been exposed to such high flow velocities, the cell may be damaged such that it is no longer viable for downstream analysis. Other systems require the use of either fixed cells or a lysis buffer to elute the cell contents. In both cases, the recovered cells are no longer viable, complicating, for example, protein analysis and it may negate the ability to subsequently culture separated cells off-chip.

Another drawback of existing systems may be an inability to enumerate cells either during or after the capture step, and/or an inability to provide optical or microscopy data on the separated fraction. In order to determine the number of separated cells, and appropriately categorize cells based on morphology and/or fluorescent tags, the ability to image the cells either during or immediately after the separation step may be important. Imaging is impractical in a number of existing systems due to the absence of a clear optical path for imaging, or capture of the cells in a high volume or across a large area that cannot be easily imaged using traditional microscopy methods, or use of high velocities that don't allow for imaging to take place due to the low residence time of positive fraction cells in the capture region.

Another drawback of existing systems may be an inability of a user to customize the capture methodology. Data from separations and analysis of the positive fraction cells may be useful in modifying or improving the capture criteria. However, existing systems to not allow for a user to customize parameters of the capture, such as the surface marker (or set of markers) used to capture positive fraction cells and other aspects of the capture methodology. For a number of existing systems, the capture methodology is fixed by the device manufacturer (for example capture onto solid substrates). Further, for systems where intrinsic physical properties of the cells determine the capture force (e.g. Sedimentation based capture, optical traps, acoustic focusing, electrophoretic phenomena, etc.) such forces may be unavailable for tuning by the user to fit the need application.

Another drawback of existing systems may be an inability to separate single cells for downstream analysis. For a number of experiment types, the positive fraction may be highly heterogeneous in nature, and much more information can be obtained through the analysis of individual cells. For example, the exact % of cells expressing a certain gene of interest can be determined using this methodology.

Another drawback of existing systems may be long run times. For various reasons (cell viability, cell settling, workflow considerations, etc) it may be important that the separation reaction be completed w/in a reasonable period of time, preferably under 1 hour, and more preferably under 15 min. For a lot of the existing systems, the full separation protocol lasts significantly longer. For example, some proposed microfluidic systems necessitate passing a full blood sample (7.5 ml) through a microscale channel of small dimensions (<1 mm). Therefore, processing the entire blood sample often takes >1 h.

Another drawback of existing systems may be that the processes are not amenable to automation. Existing systems are not compatible with standard fluid handling equipment, and, in other cases, don't have the ability to run multiple samples in parallel. Finally, the throughput and sample to sample contamination may be important issues limiting overall throughput of separation reactions.

Another drawback of existing systems may be the need for a large fluid volume and/or large dilution for the separated fraction. The volume of fluid per cell in the positive sample post separation may be an important parameter for several analysis techniques, such as genotyping via PCR. However, for existing flow-through separation methods like FACS (fluorescence activated cell sorting) use a sheath fluid that effectively dilutes the starting sample, and it may be very difficult to separate the cells of interest into volumes below a few uL per cell. More typically, the separated fraction is presented in 100's of μL volumes and above. For low cell numbers in a large background, the total volume of the positive fraction is often in the mL range.

Examples described herein relate to systems for the separation of magnetically labeled particles from fluids. Described examples may address all, some, or none of the above-described drawbacks of existing systems. The quality of separation in terms of capture efficiency, percent purity with respect to background cells, and percent recovery may be increased relative to previous techniques by using, in some examples, a combination of forces to enable separation of the biological material. Examples of the forces which may be used are magnetic forces, gravitational and inertial forces, and hydrodynamic forces. In some described examples, recovery of magnetically labeled particles may be facilitated by including a removable substrate forming a portion of a microfluidic device. Particles can be collected at the removable substrate, and then may be removed from the microfluidic device by removing the removable substrate. This may enable the separation of positive fraction cells into very small fluid volumes. Example systems may also have the ability to both enumerate particles, which may in some examples be cells, and characterize them via imaging using microscopy. Systems and methods for separating single cells and performing single cell analysis (e.g. genotyping) are also described.

Certain details are set forth below to provide a sufficient understanding of embodiments of the invention. However, it will be clear to one skilled in the art that embodiments of the invention may be practiced without various of these particular details. In some instances, well-known fluids, biological materials, buffering and washing steps, device components, circuits, control signals, timing protocols, and software operations have not been shown in detail in order to avoid unnecessarily obscuring the described embodiments of the invention.

As stated above, examples described herein relate to systems for the separation of magnetically labeled particles from fluids. Particles, as used herein, refers generally to any species that may be labeled with a magnetic label and separated in accordance with techniques described herein. Examples of particles include cells.

Fluids, as used herein, refers generally to any fluid, liquid or gas, which may present in a microfluidic device and from which particles may be separated, as described herein. Generally, fluids may also be transported through the microfluidic device. Example fluids include biological fluids including, but not limited to, blood, urine, dissociated tissue, or saliva. A biological fluid in some examples may be mixed with another fluid, such as a buffer fluid.

Magnetic label, as used herein, refers generally to any moiety having a magnetic property that may be affixed to or form a part of a particle. Generally, the magnetic label may cause a particle having the magnetic label to experience a force responsive to a magnetic field. In some examples, the magnetic labels may include beads and may be referred to as magnetic beads. Magnetic beads may be used, for example, which bind an antigen on a cell surface or other cellular component. The magnetic label may have paramagnetic properties.

Microfluidic device, as used herein, refers to a device capable of containing fluid and having at least one feature having a microscale dimension—e.g. generally less than 1 mm. Microfluidic devices are generally fabricated in accordance with microscale fabrication techniques such as, but not limited to, lithography, etching, bonding, or embossing.

Fluidic feature, as used herein, refers to any feature of a microfluidic device capable of having fluid present within the feature. Examples of fluidic features include, but are not limited to, channels, chambers, wells, reservoirs, inlet ports, and outlet ports. It is to be understood that the configuration of microfluidic devices described herein may be quite flexible, and different fluidic features may be provided to perform the functions described below in substantially any arrangement. Generally, the term 'channel' may be used to refer to a fluidic feature having a substantially longer length than width, or a fluidic feature intended to transport fluid from one region of the microfluidic device to another. The term 'chamber' may generally be used to refer to a fluidic feature having a length on the same order as the width of the fluidic feature, or a fluidic feature intended to contain a fluid for a particular phase or phases of an analysis.

Separated, separating, or separated from a fluid, as used herein, generally refers to the process of collecting the species to be separated in a particular location or directing the species to be separated in a particular direction. The species may remain physically in the fluid, but may be directed toward a particular location or collected in a particular location, in this manner, the species may be 'separated' from the fluid in the sense that it's motion has to some extent been controlled.

FIG. 1 is a flowchart illustrating a method in accordance with an embodiment of the present invention. The method 100 includes blocks 105 and 110. Block 105 recites separating, in a microfluidic device, a plurality of particles having magnetic labels from a fluid, at least in part using a magnetic force. Embodiments of microfluidic devices that may be used in separating the particles from a fluid will be described further below. Examples of systems and methods for generating the magnetic force will also be described further below. Although not shown in FIG. 1, prior to block 105, Prior to block 105, any number of sample preparation actions may occur. For example, the particles may be combined with the magnetic labels, which also may occur in the microfluidic device in some examples. Moreover, other particles (e.g. a negative fraction) may be labeled with different labels, such as labels configured to increase their sedimentation velocity, as will be described further below. Other sample preparation actions may include, separating a buffy coat from a blood sample, which may also occur in the microfluidic device.

Referring again to block 105, in some examples, another force may also be used to separate the plurality of particles having magnetic labels in block 105 instead of or in addition to the magnetic force. In some examples, a gravitational (for example, sedimentation force), inertial (for example, centrifugal), electric, drag, hydrodynamic or other force may be applied to the particles to enhance or effect separation. In some examples, a second force, such as a gravitational, electric, drag, hydrodynamic or other force, is used in addition to a magnetic force. The second force and the magnetic force may act at least partially in opposition, such that, for example, particles having a magnetic force experience a force in one direction, or a force having a component in one direction, while a second force is applied in a second direction, or with at least a component in the second direction, where the second direction is opposite to the first direction. In this manner, for example, all particles may experience a gravitational force downward, or toward a periphery of a device in a case of centrifugal force, while a magnetic force is applied to generate a magnetic force upward, or toward the center of the device in the case of centrifugal force. In other examples, two converged microfluidic streams may be flowing through the device, and the magnetic field may be applied to draw cells across the interface between the two streams, as will be described further below. Examples of device which may facilitate the application of opposing forces will be described further below.

Accordingly, in some examples, the separating recited in block 105 may be performed by sedimenting particles which are substantially free of magnetic labels while applying a magnetic force substantially opposite to a direction of the gravitational force. In some examples, the particles which are substantially free of magnetic labels may include 'heavy' labels intended to increase the sedimentation velocity of the particles.

The separation described in block 105 of FIG. 1 may occur during flow of a fluid through a microfluidic device, or may occur while the fluid is not being propelled through the device. In some examples where separation occurs at least partially while the fluid is flowing through the device, separation may occur in a low shear region of the microfluidic device, as will be described further below. This may reduce shear forces experienced by the particles during separation.

In some examples, the separating described in block 105 may be implemented by generating a magnetic field across the microfluidic device such that the plurality of particles having magnetic labels is driven toward a collection location. As will be described further below, the collection location may be a removable portion of the microfluidic device, such as a substrate reversibly coupled to an opening in a fluidic feature of the microfluidic device. In some examples, the separating described in block 105 may include positioning a magnet proximate the microfluidic device. As will be described further below, in some examples the microfluidic device may be placed into an analysis instrument configured to position the magnet proximate to the microfluidic device. In some examples, the method 100 may accordingly include positioning the magnet proximate the microfluidic device, which in some examples may include controlling the position of the magnet with pneumatic controls.

Following block 105, although not shown in FIG. 1, any number of wash steps may occur. In some examples, the particles including magnetic labels may be separated to a location within the microfluidic device and one or more wash steps may be performed to remove particles not having magnetic labels, for example.

Also following block 105, in some examples particles may be trapped in the microfluidic device. In some examples, the particles may include cells, and single-cells may be trapped through the use of a negative pressure applied to a portion of the microfluidic device. Examples will be described further below.

Also following block 105, in some examples, particles may be imaged within the microfluidic device. Examples of imaging techniques which may be used include microscopy, scanning laser microscopy, impedance measurements, or combinations thereof. Examples of microfluidic devices that may facilitate imaging of the particles in a same device in which separation occurs are described further below. In some examples, the particles may be imaged in a same location at which they were collected during the separation. Accordingly, one or more images of the particles may be generated, and may be displayed, for example, on a display device such as a monitor, screen, or data related to the image saved in, for example, a computer readable medium such as but not limited to a memory device. In some examples, data generated during imaging may be used to further characterize the particles (e.g. cells) of interest by looking at fluorescent signals, morphology or co-localization of fluorescent signals where the particles included a fluorescent moiety. In examples where particles (e.g. cells) are not immobilized during separation, such as where a continuous flow system is used, imaging may be performed while cells are moving at a slow enough rate through an imaging region of the microfluidic device, or downstream from the separation region for the positive fraction cells.

Referring again to FIG. 1, block 110 recites removing a portion of the microfluidic device containing the plurality of particles having magnetic labels. Accordingly, in some examples, microfluidic devices are provided having a removable portion to which the particles having magnetic labels may be immobilized during separation. Examples are described further below. The removable portion may include, for example, a substrate reversibly coupled to an opening in a microfluidic device substrate. In other examples, the particles having magnetic labels may be separated to a reservoir or other fluidic feature that may be removed from the microfluidic device.

Following removal of the plurality of particles in block 110 of FIG. 1, any number of analysis techniques may be performed on the removed particles. In some examples, imaging of the particles may occur after removal from the microfluidic device. For example, the portion of the microfluidic device that has been removed may be imaged using any of the techniques mentioned above. Other examples of analysis techniques include, but are not limited to, cell biomarker analysis, including but not limited to the use of, genetic, RNA, protein-based, metabolic and/or signaling biomarkers. Examples of analysis techniques include, but are not limited to, PCR, FISH sequencing, RNA analysis, protein analysis, signaling analysis, and/or phosphorylation state analysis. Example of analysis techniques further include, but not limited to, culturing of cells having magnetic labels. One or more of the following instrument platforms may be used for downstream analysis: real time PCR platforms, array based sequencing, Roche Lightcycler, Fluidigm Biomark, Raindance RDT, or the OpenArray® Real-Time PCR System. Optionally, additional sample preparation steps may be performed before the analysis steps, which may include, but are not limited to, removing negative fraction cells, segregating and analysis of single cells separately, cell lysis, or culturing of viable separated cells either on or off-chip. In some examples where the particles including magnetic labels are not removed from the microfluidic device, any of the above-mentioned analysis techniques may be performed within the microfluidic device. Examples of instruments, which are described further below, may include components to facilitate the analysis techniques described above, such as, but not limited to heating components, and/or cooling components which may facilitate PCR.

Having provided an overview of example methods according to embodiments of the present invention, examples of devices which may be used for the magnetic separation of particles from a fluid will now be described, along with examples of methods for using the devices.

FIGS. 2A-D are schematic illustrations of portions of a microfluidic device arranged in accordance with examples of the present invention. FIGS. 2A-2D are cross-sectional schematic illustrations during different points of time of the performance of an example method according to the present invention.

Figure 2A:
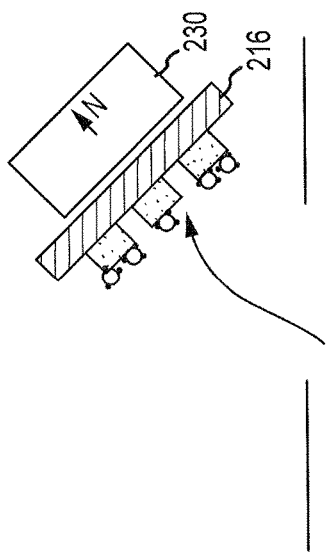
FIGS. 2A-D are schematic illustrations of portions of a microfluidic device arranged in accordance with examples of the present invention.

FIG. 2A is a schematic illustration of a portion of a microfluidic device 205 during a separation of magnetic particles from a fluid. The portion of the microfluidic device 205 includes a fluidic feature 210. The fluidic feature 210 may be a channel or a chamber that may be provided in a substrate. The substrate may generally be any suitable material for use with the fluid to be contained in the fluidic feature. Examples of substrates include, but are not limited to, glass, thermoplastic, polydymethylsiloxane (e.g. PDMS), elastomer, or silicon. The substrate may be coated with generally any material and may be functionalized as understood in the art. A fluid may be present in the fluidic feature 210. The fluid in some examples may flow through the fluidic feature 210 in a direction indicated by arrows 212. The fluidic feature 210 includes an opening 214 in a wall of the fluidic feature 210. The opening 214 may allow for placement of another substrate 216 reversibly coupled to the fluidic feature 210. Accordingly, the substrate 216 may seal the fluidic feature 210 sufficiently to flow a fluid through the feature and/or contain a fluid within the feature during separation. However, the substrate 216 may subsequently be removed, as will be described further below.

The fluid contained in and/or passed through the fluidic feature 210 may, as described above, contain particles having magnetic labels. The particles 217-221 having magnetic labels are shown in FIG. 2A. The magnetic labels are shown as dots, such as the labels 222, 223, 224 on the particle 221. Although three magnetic labels are shown for each particle in FIG. 2A, any number may be used. Other particles may be present in the fluid within the fluidic feature 210 which do not have magnetic labels. For example, the particles 225-228 shown in FIG. 2A do not have magnetic labels. Generally, the particles of interest are referred to as a 'positive fraction' while the particles not of interest are referred to as a 'negative fraction'. Depending on the analysis desired, either particles with the magnetic labels, or those without may be the 'positive fraction.'

A magnet 230 may be placed proximate the microfluidic device, as shown in Figure A. The magnet 230 may be separate from the microfluidic device or may be integrated into the microfluidic device itself. The magnet 230 may generate a magnetic field or magnetic field gradient across the fluidic feature 210, which may drive the particles containing magnetic labels toward the substrate 216. Although shown coupled to the substrate 216 in FIG. 2A, the magnet may be separate from the substrate 216, or in some examples, a magnet of opposite polarity may be placed on the opposite side of the fluidic feature 210 to drive particles toward the substrate 216. Any suitable magnet may be used, including permanent and electromagnets.

Regions of the substrate 216 may be functionalized, as shown as regions 232 in FIG. 2A. In other examples, however, the functionalized regions 232 may not be provided. The functionalized regions 232 may facilitate the particles having magnetic labels being immobilized at the substrate 216 by, for example, binding to the particles. For example, a regularly spaced array of cells may be obtained by spacing the functionalized regions appropriately, greatly improving imaging clarity. If the surface is functionalized to selectively bind cells of interest, other contaminating cell fractions may be removed more easily during the wash step or elution step post separation. The opposite effect may also be desirable, with surfaces functionalized to prevent tight binding of separated cells and enhance elution after the removal of magnetic forces. The substrate 216 may in some examples be patterned with features to ease counting of collected particles, similar to the lines and squares used on hemacytometers.

Figure 2C:
Figure 2B:
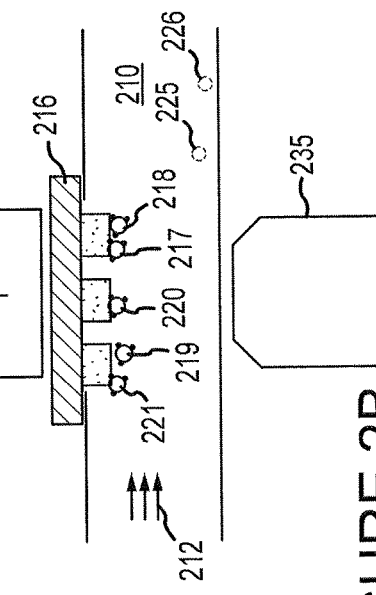

FIG. 2B is a cross-sectional illustration of the fluidic feature 210 during a wash phase of a method in accordance with an embodiment of the present invention. Following separation, the particles 217-222 may be immobilized at the substrate 216, including at the functionalized regions 232 in embodiments where functionalized regions are present. A buffer fluid may be provided in the fluidic feature 210 and/or flowed through the fluidic feature 210 as indicated by the arrows 212. In some examples, the buffer fluid may flow in the opposite direction. Accordingly, particles without magnetic labels may flow through or otherwise be removed from the fluidic feature 210. Accordingly, particles 227 and 228 are no longer shown in FIG. 2B and the particles 225 and 226 have moved further along the fluidic feature 210 relative to their position in FIG. 2A. The particles, immobilized at the substrate 216, may be imaged within the fluidic feature 210, for example, by providing an objective 235 on an opposite side of the fluidic feature 210 from the substrate 216. In some examples, the magnet 230 may be removed, and a microscope objective may be placed in the position shown by the magnet 230 in FIG. 2B. In such embodiments, the substrate 216 may preferably be at least partially optically transparent.

FIG. 2C is a cross-sectional illustration of the fluidic feature 210 in accordance with an embodiment of the present invention illustrating how the captured particles may be removed from the microfluidic device. As shown in FIG. 2C, the substrate 216 may be removed from the microfluidic device. While shown being removed along with the magnet 230, in other embodiments the magnet 230 may not be coupled to the substrate 216 and/or may not be removed with the substrate 216. In some embodiments, the magnet 230 may be moved away from the microfluidic device prior to removing the substrate. As will be described further below, in some examples, the magnet may be coupled to a movable mechanism and/or pneumatic controls which may control movement of the magnet 230 and/or the substrate 216. The particles without magnetic labels may have been completely removed from the fluidic feature during, e.g. the wash step shown in FIG. 2B, or may remain in the feature as shown in FIG. 2C.

Figure 2D:
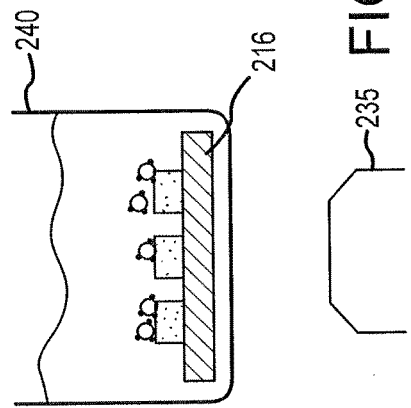

FIG. 2D is a schematic cross-sectional illustration of the substrate 216 as placed into another receptacle for subsequent analysis. The substrate 216 along with immobilized particles having magnetic labels may be transported for subsequent analysis. In FIG. 2D, the substrate 216 is shown in a vessel 240 after decoupling from the magnet 230. In other embodiments, the substrate 216 may be coupled to a different fluidic feature of the same or a different microfluidic device. In still other embodiments, the particles having magnetic labels may be removed from the substrate 216 and placed in another vessel or microfluidic device for analysis. The particles may, for example, be imaged by providing a microscope objective 235 in a position to image the particles in the vessel 240. The vessel 240 may be any of a variety of vessels used in analysis techniques, including, but not limited to, a PCR tube, a well on a PCR plate, a cell culture well, a histology slide, a FISH substrate, a micromanipulator platform, or a microdisection substrate.

Figure 3A:
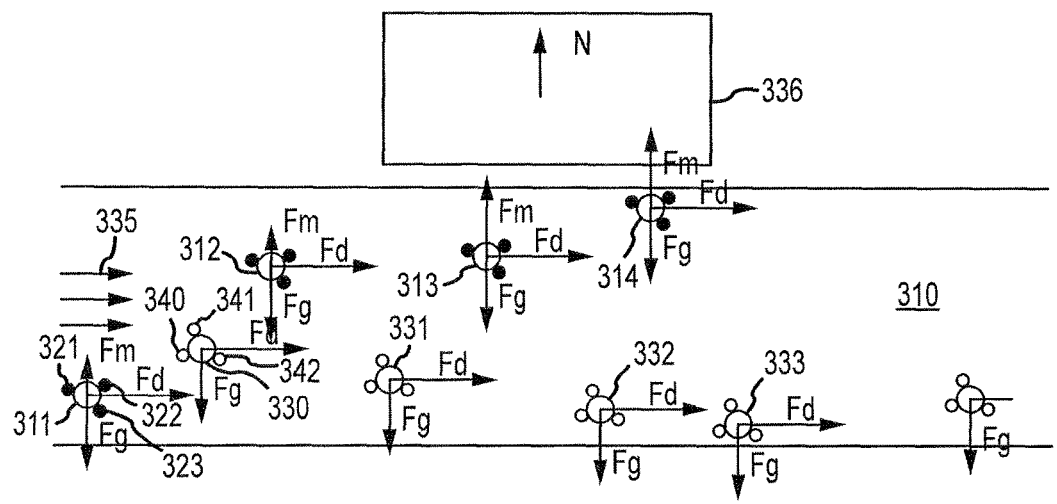
FIGS. 3A and 3B are schematic illustrations of portions of a microfluidic device arranged in accordance with examples of the present invention.
Figure 3B:
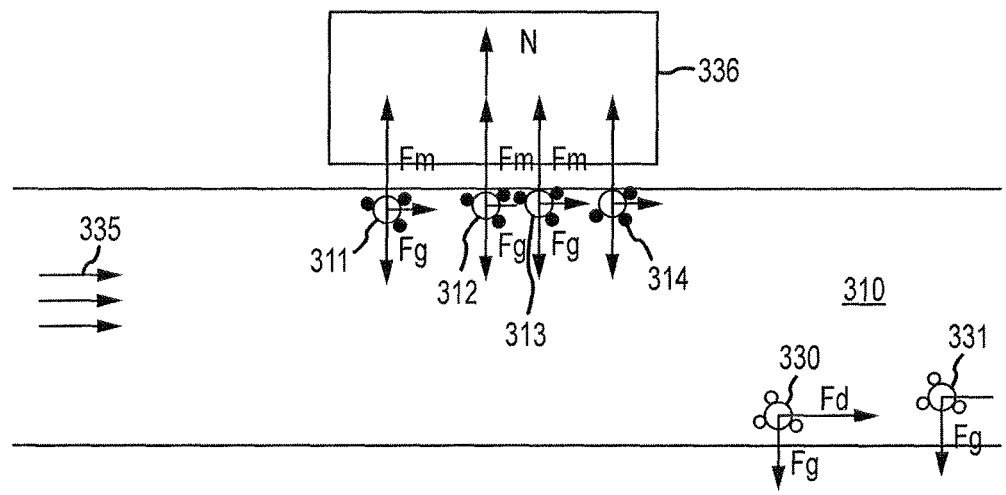

As mentioned above, divergent forces may be used to facilitate separation of particles having magnetic labels from a fluid. FIGS. 3A and 3B are schematic illustrations of portions of a microfluidic device arranged in accordance with examples of the present invention. FIG. 3A is a cross-sectional schematic illustration of a fluidic feature 310. The fluidic feature 310 as shown does not include an opening as described above with reference to FIGS. 2A-D, however, the mechanisms described here with reference to FIGS. 3A and 3B may be used by devices in the embodiments shown in FIGS. 2A-2D.

In FIG. 3A, particles 311-314 having magnetic labels are shown. The magnetic labels are shown as dots, such as the magnetic labels 321-323. Although three magnetic labels are shown on each particle, any number may be used. Particles 330-333 are also present in the fluidic feature 310 but do not include a magnetic label. During operation, a fluid containing the particles may be flowed through the fluidic feature in the direction shown by arrows 335. A magnet 336 is provided proximate the microfluidic device as shown, such that a magnetic field or magnetic field gradient may be generated across the fluidic feature 310. The particles 311-314 having the magnetic labels accordingly may feel a magnetic force driving the particles 311-314 toward the magnet 336. In other examples where the polarity is different, the force may drive the particles away from the magnet 336. The magnetic force experienced by each particle is shown by a vector in FIG. 3A labeled $F_m$. Note that the particles which do not include a magnetic field experience do not experience a magnetic force driving them toward or away from the magnet 336. Other forces include a drag force on the particles due to the fluid flow, which is represented as forward arrows $F_d$ in FIG. 3A. The drag force experienced by a particle may be related to the particles size and/or geometry. In other examples, the opposite direction of flow may be used. The particles all also experience a gravitational force, shown in FIG. 3A as $F_g$. The gravitational force may be related to the mass and density of a particle. Accordingly, the geometry of the fluidic feature 310, the strength of the magnet 336, and/or the rate of flow may be selected such that the magnetic forces on the particles 311-314 are sufficient to drive the particles toward the magnet 336 during the time the particles 311-314 are resident within the fluidic feature 310. Moreover, the size of the fluidic feature 310 and/or the rate of flow may be selected to ensure the particles 330-333 have sedimented or partially moved out of the flow during the time the particles 330-333 are resident in the fluidic feature 310.

In some examples, the gravitational force shown in FIG. 3A may simply be due to the innate mass and/or density of the particles. However in other examples, the particles 330-333 may be labeled with a non-magnetic label intended to increase the mass and/or density of the label-bound particles 330-333 to enhance sedimentation. The non-magnetic labels are shown as small circles such as the labels 340-342 in FIG. 3A. The non-magnetic labels may be implemented, for example, as beads, and may be selected to bind to the particles 330-333 which may be the 'negative fraction.'

FIG. 3B illustrates a schematic cross-section of the fluidic feature 310 during a wash phase. During the wash phase, the particles 311-314 are held at an edge of the fluidic feature 310 by the magnetic force generated by the presence of the magnet 336, while the particles 330-333 may be flowed downstream. The particles 330 and 331 are shown remaining in the fluidic feature 310 in FIG. 3B, but are either already flowing downstream or may also later be flowed downstream.

In this manner, a second force (e.g. gravitational force), may be used to aid in the separation of a positive fraction from a negative fraction, which may increase the final purity of the separated sample or shorten the time required for separation. The second force may act on particles either before, during, or after the residence inside the fluidic feature 310. While gravitational force has been used as an example of such a second force with reference to FIGS. 3A and 3B, other forces may be used, such as, but not limited to, electrical, inertial, drag forces, optical forces (e.g. optical tweezers), or diamagnetic forces. In one example, the particles 330-333 may include diamagnetic beads which, when placed in a magnetic field, may experience forces opposite to the forces acting on paramagnetic labels bound to the particles 311-314. The principle of divergent force separation described with reference to FIGS. 3A and 3B may also apply to examples utilizing a removable portion of a microfluidic device, such as those shown in FIGS. 2A-2D.

Figure 4A:
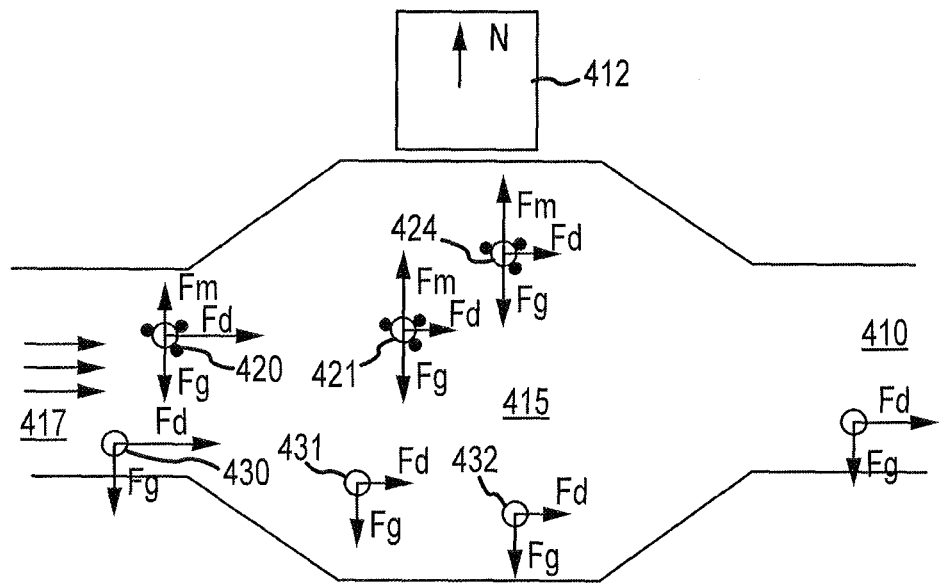
FIGS. 4A and 4B are schematic illustrations of cross-sections of a portion of a microfluidic device arranged in accordance with an embodiment of the present invention.
Figure 4B:
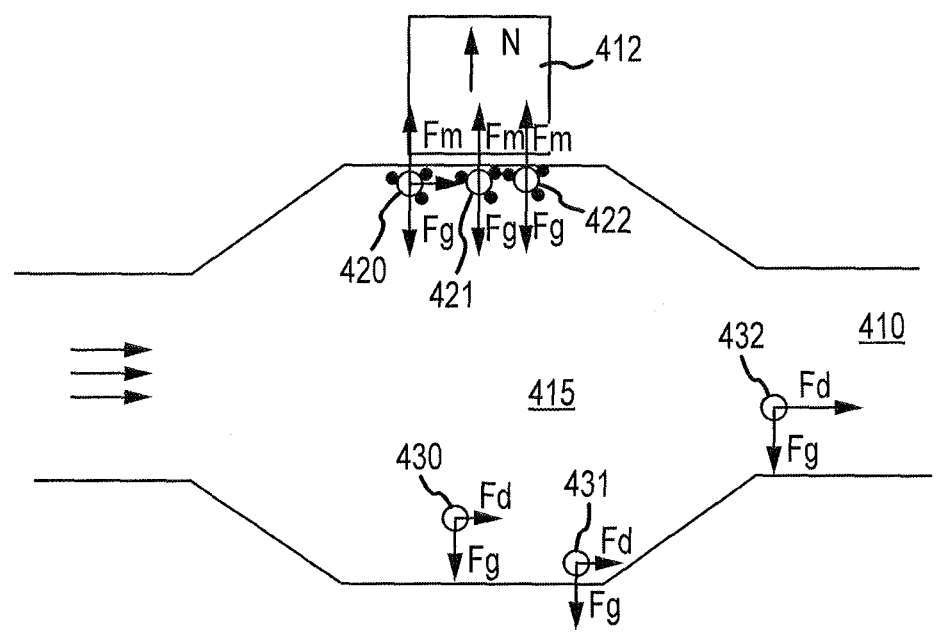

FIGS. 4A and 4B are schematic illustrations of cross-sections of a portion of a microfluidic device arranged in accordance with an embodiment of the present invention. A cross-section of a fluidic feature 410 is shown. A magnet 412 may be provided proximate the microfluidic device in a region 415 of the fluidic feature 410 having a larger cross-sectional dimension than a neighboring region 417 of the fluidic feature. The region 415 may accordingly have a lower velocity of flow as compared to the velocity in the region 417 feeding into the region 415, because flow velocity may be determined in part by the cross-sectional area of the region. Accordingly, residence time of particles in the region 415 proximate the magnet 412 may be lengthened. Accordingly, the time for the magnetic force to act on the particles having magnetic labels (and divergent forces to act on the other fraction) may also be increased. Moreover, particles may experience diminished drag forces and shear forces in region 415. Drag forces generally oppose forces of separation, so reduced drag forces may enhance separation. Still further, shear forces may contribute to the loss of cell viability. Accordingly, reducing shear forces may increase cell viability. A wide region of a fluidic feature may also be used in conjunction with any of the embodiments of devices or methods described herein. As shown in FIG. 4A, particles 420-422 may be flowed into the region 415 from the region 417. The particles 420-422 may experience a magnetic force toward the magnet 412. Particles 430-432 may not experience a magnetic force and may simply flow through the region 415, and/or may sediment out if gravitational forces are also present. FIG. 4B is a schematic cross-section illustrating the fluidic feature 410 during a wash phase. During a wash phase, the particles 420-422 may be immobilized in a vicinity of the magnet 412 while the particles 430-432 are flowed through the region 415 out of the fluidic feature 410. Recall that, because the particles 420-422 are resident in the region 415 during this wash phase, they may experience reduced shear forces relative to an embodiment where the region 415 did not have a larger cross-sectional dimension than a neighboring region. In FIGS. 4A and 4B the region 415 is drawn as having a larger cross-sectional height than a neighboring region, however, any or all cross-sectional dimensions may be modified—height, width, or depth in accordance with embodiments of the present invention. Moreover, the increased cross-sectional height shown in FIGS. 4A and 4B is implemented using straight slanted walls entering the region 415. In other embodiments, curved or abrupt changes in dimension may be used.

Figure 5:
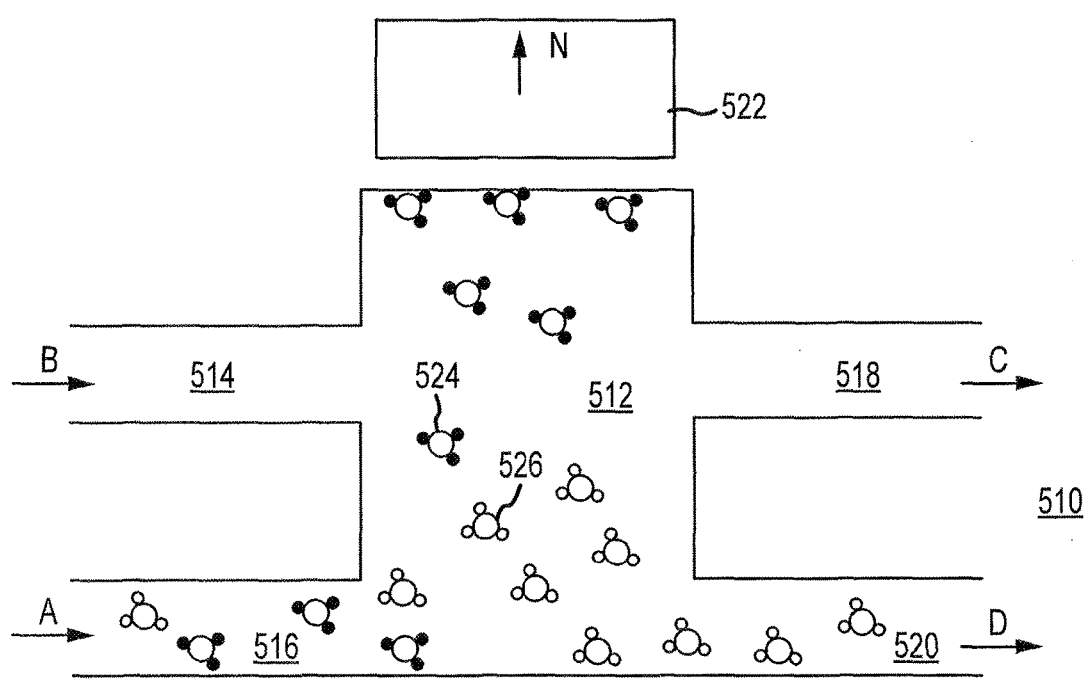
FIG. 5 is a schematic cross-section of a portion of a microfluidic device in accordance with an embodiment of the present invention

FIG. 5 is a schematic cross-section of a portion of a microfluidic device in accordance with an embodiment of the present invention. A cross-section of a portion of a microfluidic device 510 is shown. The cross-section includes a low shear region 512 of a fluidic feature. As described above, the low shear region 512 has a larger cross-sectional dimension than regions 514 and 516 neighboring the low shear region 512. In the example shown in FIG. 5, the regions 514 and 516 may be channels while the low shear region 512 may be a chamber, although any fluidic features may be used. The low shear region 512 may also have a larger cross-sectional dimension than the neighboring regions 518 and 520, shown as outlet channels from the region 512 in FIG. 5. A magnet 522 may be provided proximate the microfluidic device to generate a magnetic field across the low shear region 512. During operation, a fluid containing particles may enter the low shear region 512 from the region 516, as shown. The fluid may contain particles including magnetic labels, such as the particle 524, and particles without magnetic labels, such as the particle 526. As described above, the particles without magnetic labels may include a non-magnetic label. The particles including magnetic labels may be separated in a portion of the region 512 nearest the magnet 522. Particles which do not include a magnetic label may exit the region 512 through the feature 520. In some examples, a buffer or other fluid may be flowed into the region 512 through the fluidic feature 514. Accordingly, particles including magnetic labels may be drawn across the flow of buffer fluid by a magnetic force. Drawing the particles including magnetic labels across a flow of buffer fluid may be advantageous in that it may provide some washing of the particles thus removing particles without magnetic labels, thus improving the purity of the separated particles. In some examples, the magnetic field may be reduced or turned off, such as by removing the magnet, after separation and washing out of the particles not including magnetic labels. The collected particles including magnetic labels may then be collected by flowing them out of the region 512.

Figure 6A:
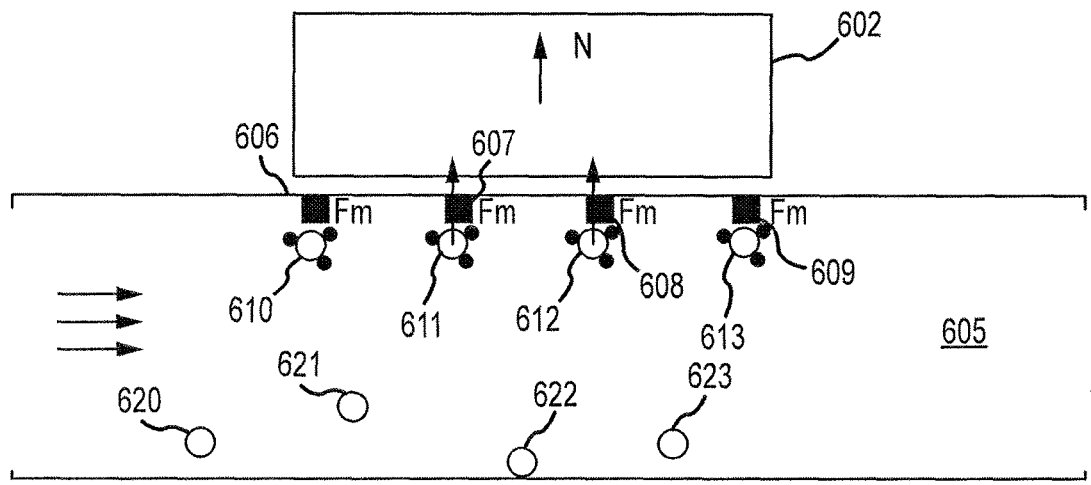
FIGS. 6A and 6B are a schematic cross-section and top-down view, respectively, of a portion of a microfluidic device arranged in accordance with an embodiment of the present invention.
Figure 6B:
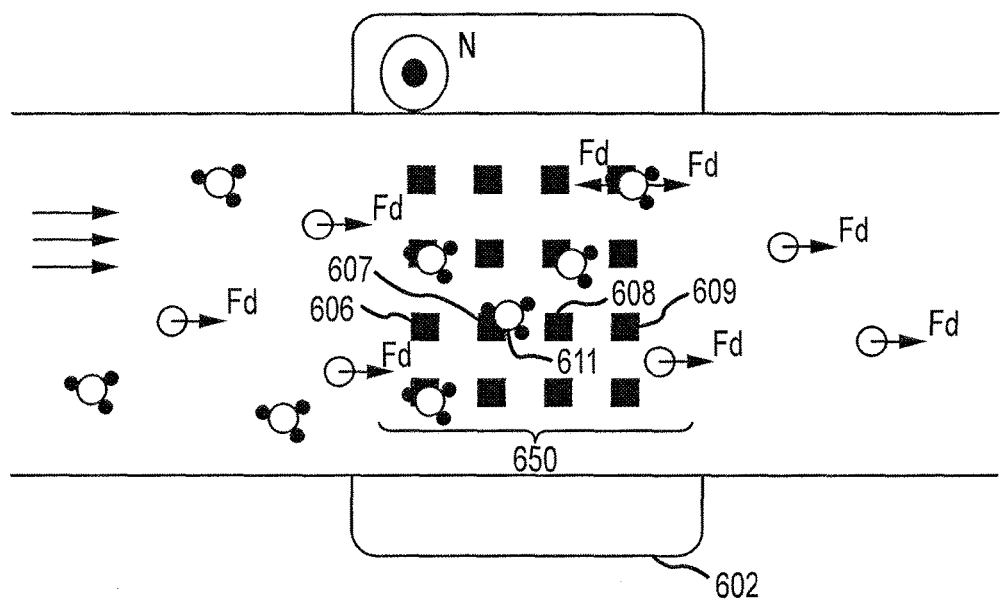

FIGS. 6A and 6B are a schematic cross-section and top-down view, respectively, of a portion of a microfluidic device arranged in accordance with an embodiment of the present invention. Structures to enhance a magnetic field gradient are provided in the examples of FIGS. 6A and 6B. In FIG. 6A, a cross-section of a fluidic feature 605 is shown. Magnetizable structures 606-609 are provided on a wall of the fluidic feature 605. Although shown as integral with the microfluidic device 605 in FIG. 6A, the magnetizable structures 606-609 may be provided outside the microfluidic channel 605 in other examples. The magnetizable structures 606-609 are paramagnetic or permanently magnetic structures that are intended to increase the magnetic field generated by the magnet 602 proximate the magnetizable structures. Accordingly, a magnetic field gradient may be stronger in locations proximate the magnetizable structures 606-609, and the particles including magnetic labels may be preferentially separated to these locations. As shown in FIG. 6A, the particles including magnetic labels 610-613 have been separated to the magnetizable structures 606-609, while other particles 620-623 not including magnetic labels have sedimented to a bottom of the fluidic feature 605. Generally, a force on particles including magnetic labels may be proportional to the magnetic field gradient and accordingly may be enhanced by the presence of magnetic structures either in or around the fluidic feature 605. Higher forces may be advantageous because they may shift the equilibrium balance between magnetic forces acting on the cells and drag forces due to fluid flow. The efficiency of separation may therefore be increased, allowing the system to operate using, for example, smaller field strengths, smaller numbers of particles having magnetic labels, smaller magnetic moments of magnetic labels and/or higher flow velocities than systems which do not include the magnetizable structures Moreover, magnetizable structures that concentrate a magnetic field at particular set of locations may allow for the capture of particles at particular locations, and/or the capture of single particles, such as single cells. As shown in FIG. 6A, the magnetizable structures 606-609 are sized and structured to capture respective single particles 610-613. FIG. 6B provides a top-down view of the fluidic feature 605. As shown in FIG. 6B, magnetizable structures may be provided in an array 650, including the structures 606-609 as shown. FIG. 6B is shown at a time when the particle 611 has been trapped on the structure 607, but the particles 610, 612, and 613 have not yet been trapped. Additional particles including magnetic labels have been trapped on other magnetizable structures shown in FIG. 6B. In some examples, following a sufficient separation time, particles including magnetic labels may be trapped at a majority of the magnetizable structures in the array 650. The array of particles, which may be an array of cells, may be advantageous for imaging and analyzing the particles, at least in part because the particles may not overlap in the field of view. The particles may, for example, be imaged in the array formation shown in FIG. 6B. It should be understood that the examples shown and described relative to FIGS. 6A and 6B may be used in combination with any of the embodiments described above, including a removable portion of the microfluidic device (e.g. magnetizable structures may be provided on or proximate to a removable portion of the microfluidic device), low shear regions, divergent forces, or combinations thereof.

FIGS. 7A-D are schematic illustrations of cross-sections of portions of microfluidic devices arranged in accordance with embodiments of the present invention. The microfluidic device of FIG. 7A includes fluidic feature 705 including a low shear region 706, a removable portion 708, and a magnet 710 proximate the removable substrate 708. Note that the removable portion 708 of the microfluidic device is positioned to collect particles having magnetic labels in the low shear region, as fluid is flowed through the fluidic feature 705 in the direction shown by the arrow. The low shear region 706 may have a larger cross-section compared with the portion of the fluidic feature 705 adjacent the region 706, where fluid flow is indicated by the arrow. Separation may accordingly be enhanced by increasing residence time in the region 706, which may also be a region where magnetic force is highest, as it is closest to the magnet 710. Moreover, the configuration shown in FIG. 7A may reduce the drag forces on separated particles as a percent of the magnetic force, and may reduce shear forces on immobilized particles on the removable substrate.

The microfluidic device of FIG. 7B includes fluidic feature 712 including low shear region 714, a removable substrate 716, and a magnet 718. The low shear region 714 may provide advantages analogous to those described above with reference to FIG. 7A. In the embodiment of FIG. 7B, the removable substrate 716 is deformable. That is, the removable substrate 716 may be flexible and configured to deform into the low shear region 714, as shown. In this manner, pneumatic pressure may be applied to a region above the substrate 716 (such as the region 720 shown in FIG. 7B) to urge the substrate 716 to deform into the region 714, which may aid in sealing the substrate 716 to the remainder of the microfluidic device, for example, at the corners 721 and 722. Accordingly, contact and sealing at edges of the substrate 716 may be controlled, which may enhance sealing and make removal of the substrate gentler on separated particles, such as cells.

The microfluidic device shown in FIG. 7C includes a fluidic feature 730 having a low shear region 732, removable substrate 734, and magnet 736, examples of which components have been described above. A magnetizable structure 738 is provided between the magnet 736 and the removable substrate 734. Note that the magnetizable structure 738 covers only a portion of the removable substrate 734, which may constrain the region in which particles may be immobilized, and may keep particles away from edges of the substrate 734. The may be advantageous because, at the edges of the substrate 734, shear forces may damage particles, such as cells, during removal of the substrate 734 from the microfluidic device.

The microfluidic device shown in FIG. 7D includes a fluidic feature 740 having a low shear region 742, and a magnet 746, examples of which components have been described above. In the example of FIG. 7D, a removable substrate 748 is provided having a form factor of a cup. That is the removable substrate 748 defines a receptacle 749 for receiving immobilized cells on one side of the removable substrate 748 and a receptacle 750 for receiving the magnet 746 on an opposite side of the removable substrate 748. In some examples, only one of the illustrated receptacles may be present. The receptacles may be advantageous in some embodiments in that, upon removal the substrate 748 from the microfluidic device, the receptacle 749 may retain fluid via surface tension forces, which may minimize damage to the particles, such as cells, which may increase cell viability. Moreover, a separate receptacle may not be required for later sample processing or analysis. That is, analysis of the particles may occur within the receptacle 749 following removal from the microfluidic device. Yet another advantage is that the magnet may be localized, that is, separated from edges of the substrate 748, and the immobilized particles may therefore be kept away from the edges of the substrate, some benefits of which were mentioned above.

Figure 8A:
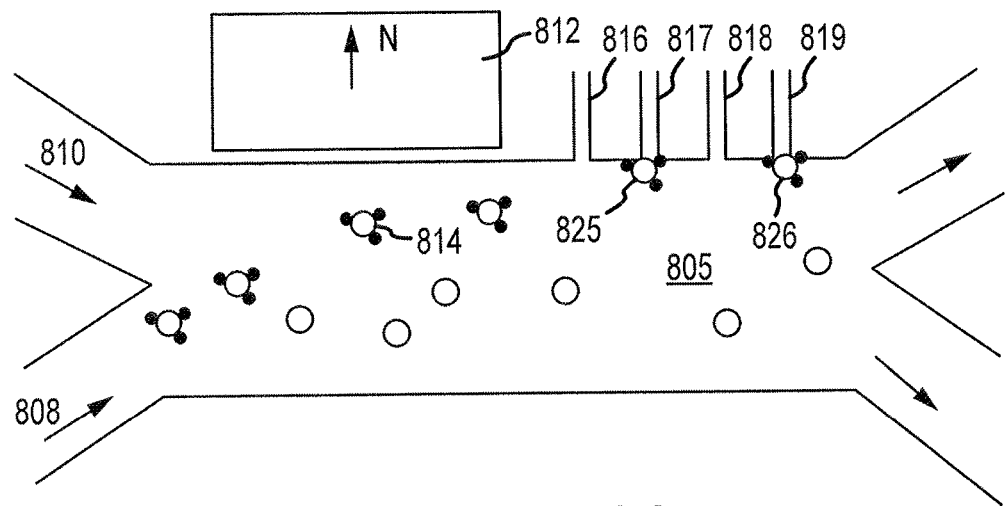
FIGS. 8A and 8B are schematic illustrations of cross-sections of portions of a microfluidic device arranged in accordance with an embodiment of the present invention.
Figure 8B:
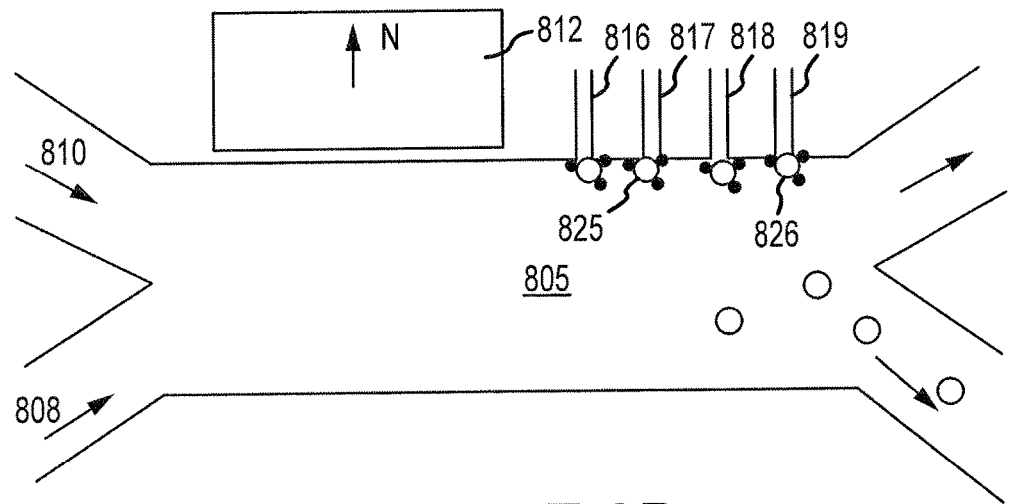

Embodiments of the present invention include devices and methods that may trap individual particles, such as individual cells, at predetermined location. Individual particles may be trapped at particular magnetizable structures, as was described above with reference to FIGS. 6A and 6B, for example. FIGS. 8A and 8B are schematic illustrations of cross-sections of portions of a microfluidic device arranged in accordance with an embodiment of the present invention. The microfluidic device shown in FIGS. 8A and 8B is configured to hydronamically trap particles whose trajectory may be controlled in part by a magnetic force. In FIG. 8A, a cross-section of a fluidic feature 805 is shown. A fluid containing particles may be flowed through the fluidic feature 805 originating from a region 808, in a direction indicated by the arrow in region 808. A buffer or other fluid may also be flowed through the region 805 introduced from a region 810 in a direction indicated by the arrow in the region 810. A magnet 812 may be provided proximate the fluidic feature 805 and may exert a magnetic force on particles including a magnetic label. Note, as has been described above with reference to FIG. 5, the particles including magnetic labels may be driven toward the magnet 812 across an interface of fluids from the regions 808 and 810. This may provide additional washing or purification of the collected particles. The magnitude of the force, flow rate, and dimensions of the fluidic feature 850 may be selected such that the particles including magnetic labels, such as the particle 814 are driven toward the magnet 812, but may not be immobilized in a region near the magnet 812, as has been described above. Instead, the particles including magnetic labels may be simply paced into a flow of the buffer or other fluid originating from the region 810 and directed toward a plurality of trapping channels 816-819.

The trapping channels 816-819 may be fluidic features which are in fluidic communication with the fluidic feature 805 as shown. The trapping channels may have a smaller cross-sectional dimension than a diameter of particles containing magnetic labels, such as smaller than a cell diameter. A lower pressure may be provided at one or more of the trapping channels 816-819 relative to a pressure in the fluidic feature 805, which may trap individual particles at the entrance to the respective trapping channel, such as particles 825 and 826. Comparatively lower magnetic forces may be needed to effect separation and immobilization of the sample in the examples shown in FIGS. 8A and 8B.

A further advantage may be that, during any wash steps, it will become much harder to remove the target cells from the trapping sites, as hydrodynamic forces are preventing movement in addition to magnetic and other forces. FIG. 8B is a schematic cross-section of the fluidic feature 805 during a wash phase. The particles including magnetic labels, such as the particles 825 and 826, are held at the openings of the trapping channels by the pressure difference between the trapping channels and the fluidic feature in addition to the magnetic forces provided by the magnet 812. If desired, positive pressure may be applied to the trapping channels 816-819 in order to release the particles and move them downstream. It should be understood that such a methodology may be used in combination with the use of a removable substrate. For example, the trapping channels may be an integral part of a removable substrate. Moreover, the embodiments of FIGS. 8A and 8B may be used in combination with any of the features described above. In some examples, the trapping channels 816-819 have a cross-sectional diameter smaller than the diameter of a positive fraction of particles of interest to be held at the trapping channels, but larger than a negative fraction intended to be flowed out of the region 805, such the negative fraction may enter the trapping channels 816-819 and be collected at a reservoir or other feature in fluidic communication with the trapping channels 816-819. In addition to intrinsic size differences between particle types, beads may be bound to the positive fraction to increase their effective cross sectional area, making this approach more viable in some embodiments.

Trapping channels may also offer the opportunity to sequester single particles, such as cells, and isolate single cells that are part of the positive fraction for downstream analysis. Each of the trapping channels 816-819, for example, may be in fluidic communication with a different fluidic feature, either on or off the microfluidic device, for isolating either the a single cell or the contents of a single cell. That is, once trapped at the entrance to the trapping channels 816-819, the individual cells may be analyzed. In some examples, a negative pressure pulse may be applied to one or more of the trapping channels 816-819 to pull particles, such as cells, into the trapping channel. In some examples, trapped cells may be lysed while under negative pressure, which may cause the contents to be eluted into the trapping channel and delivered to an analysis location. In some examples, these techniques may be used to interrogate individual circulating tumor cells for analysis. In general, separated cells may be part of a heterogeneous population, so cell-to-cell differences may be an important parameter. For example, genetic mutations and expression profile changes may be present in some but not all of the captured cells. Examples of features shown and described herein allow for detection of these cell-to-cell differences.

Accordingly, examples of portions of microfluidic devices have been described above that may include features for separating particles from a fluid suspension using magnetic forces. Removable portions of microfluidic devices, the use of divergent forces, low shear regions, magnetizable structures for field focusing, trapping channels, and combinations thereof have been described. These features may be included in substantially any microfluidic device configuration, where the complete microfluidic device may include a variety of additional fluidic features for routing and/or containing fluid and performing additional sample preparation and/or analysis operations. Examples of microfluidic device will now be further described.

Figure 9:
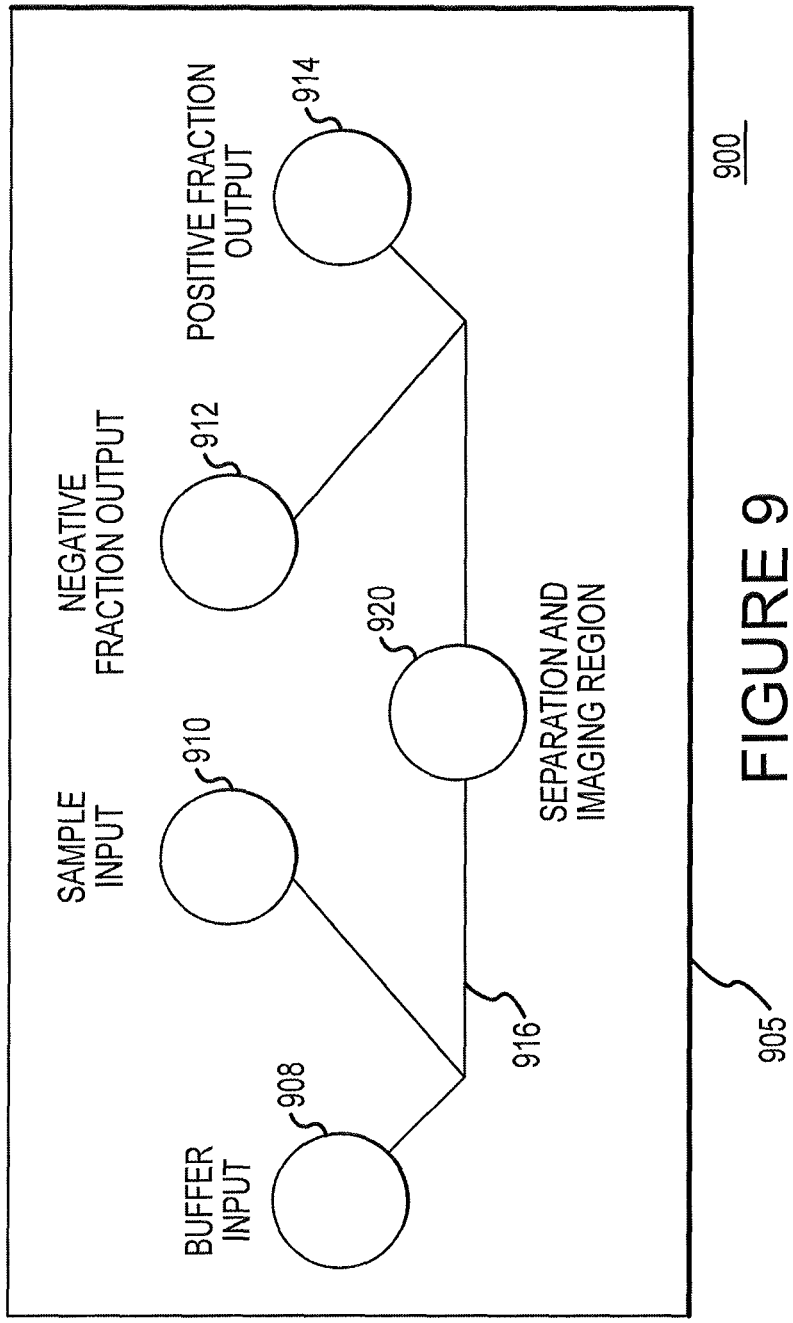
FIG. 9 is a schematic illustration of a top-down view of a microfluidic device arranged in accordance with an embodiment of the present invention.

FIG. 9 is a schematic illustration of a top-down view of a microfluidic device arranged in accordance with an embodiment of the present invention. The microfluidic device 900 includes a substrate 905 which at least in part defines several fluidic features. Input/output ports 908, 910, 912, and 914 are provided to deliver fluids to or from a channel 916. The input port 908, for example, may be used to provide a buffer fluid to the channel 916. The input port 910, for example, may be used to provide a sample containing particles to the channel 916. The output port 912, for example, may be used to collect a negative fraction of particles from the channel 916. The output port 914, for example, may be used to collect a positive fraction of particles, e.g. particles including a magnetic label, from the channel 916. It is to be understood that the number, location, and function of input and/or output ports is very flexible, and other numbers, locations, and functions may be provided in other embodiments. For example, in some embodiments, as has been described above, particles may be immobilized or trapped within the microfluidic device, and in some examples a portion of the microfluidic device containing the immobilized or trapped particles may be removed. Accordingly, it may not be necessary in all embodiments to have both the outlet ports 912 and 914. A separation and/or imaging region 920 is provided in fluid communication with the channel 916. The separation and/or imaging region 920 is intended to identify a location of the microfluidic device 900 where separation may occur, and any fluidic feature may be provided in this location, including any of the fluidic features described above. In the example of FIG. 9, it is contemplated that separation and imaging may occur in the same general region, but in other embodiments the separation and imaging regions may be separated.

Figure 10:
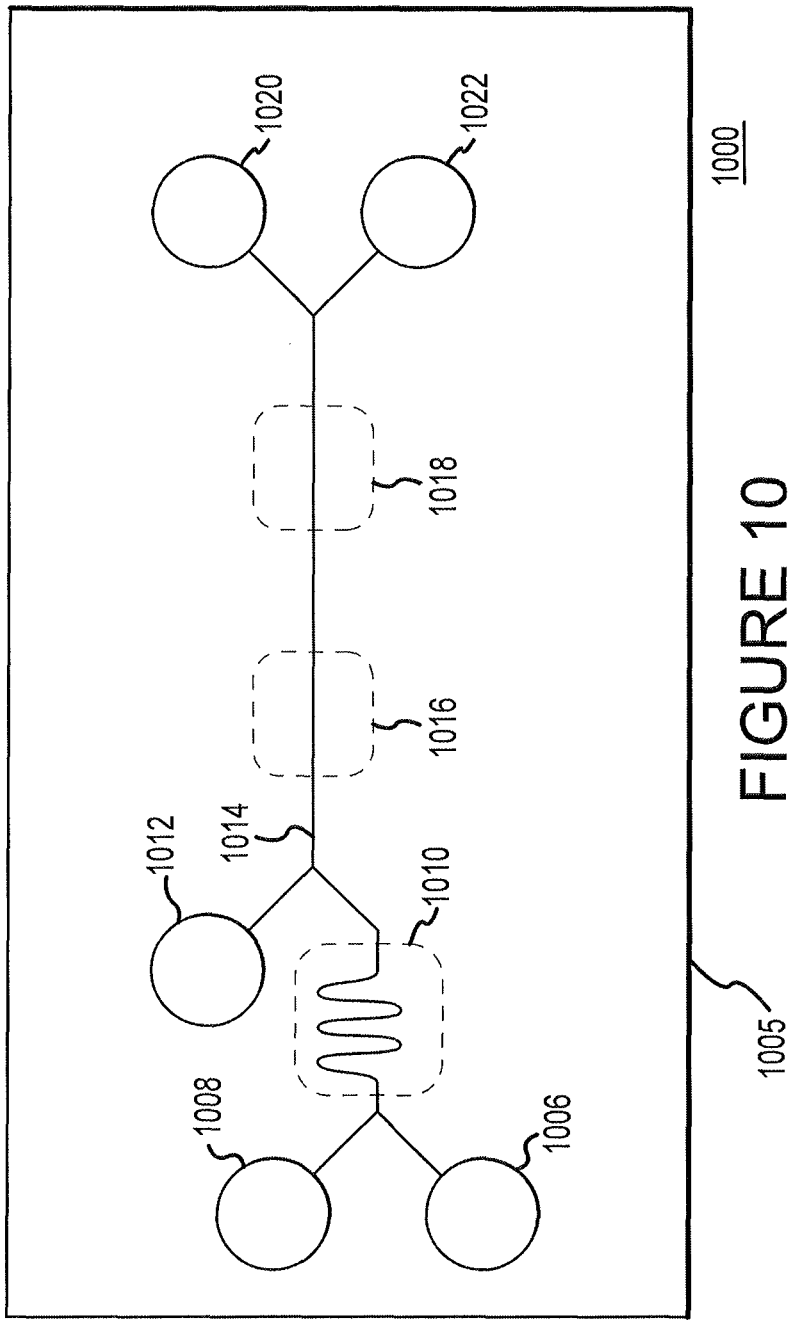
FIG. 10 is a schematic illustration of a top-down view of another microfluidic device arranged in accordance with an embodiment of the present invention.

FIG. 10 is a schematic illustration of a top-down view of another microfluidic device arranged in accordance with an embodiment of the present invention. The microfluidic device 1000 includes a substrate 1005 that may in part define the features shown. An input port 1006 may be provided for input of labels, such as beads. The labels may be magnetic labels, as described above. An input port 1008 may be provided for input of a sample including particles. A region 1010 may be provided in the microfluidic device 1000 for labeling certain particles in the sample received from the input port 1008 with the labels received from the input port 1006. The region 1010 may include, for example, a winding channel as shown to allow for sufficient residence time for labeling, or a chamber, or substantially any other fluidic feature. Another input port 1012 is provided for introduction of a buffer fluid to a channel 1014. The channel 1014 may accordingly receive a buffer fluid from the input port 1012 and fluid containing labeled particles from the region 1010. A separation region 1016 and imaging region 1018 are provided along the channel 1014 which may be regions for performing any of the separation techniques and/or analysis techniques described above, and the regions 1016 and 1018 may in some examples be combined. Two outlet ports 1020 and 1022 may be provided, which may be intended to collect a respective positive and negative fraction in some examples, but in other examples, one or both may not be necessary.

Figure 11:
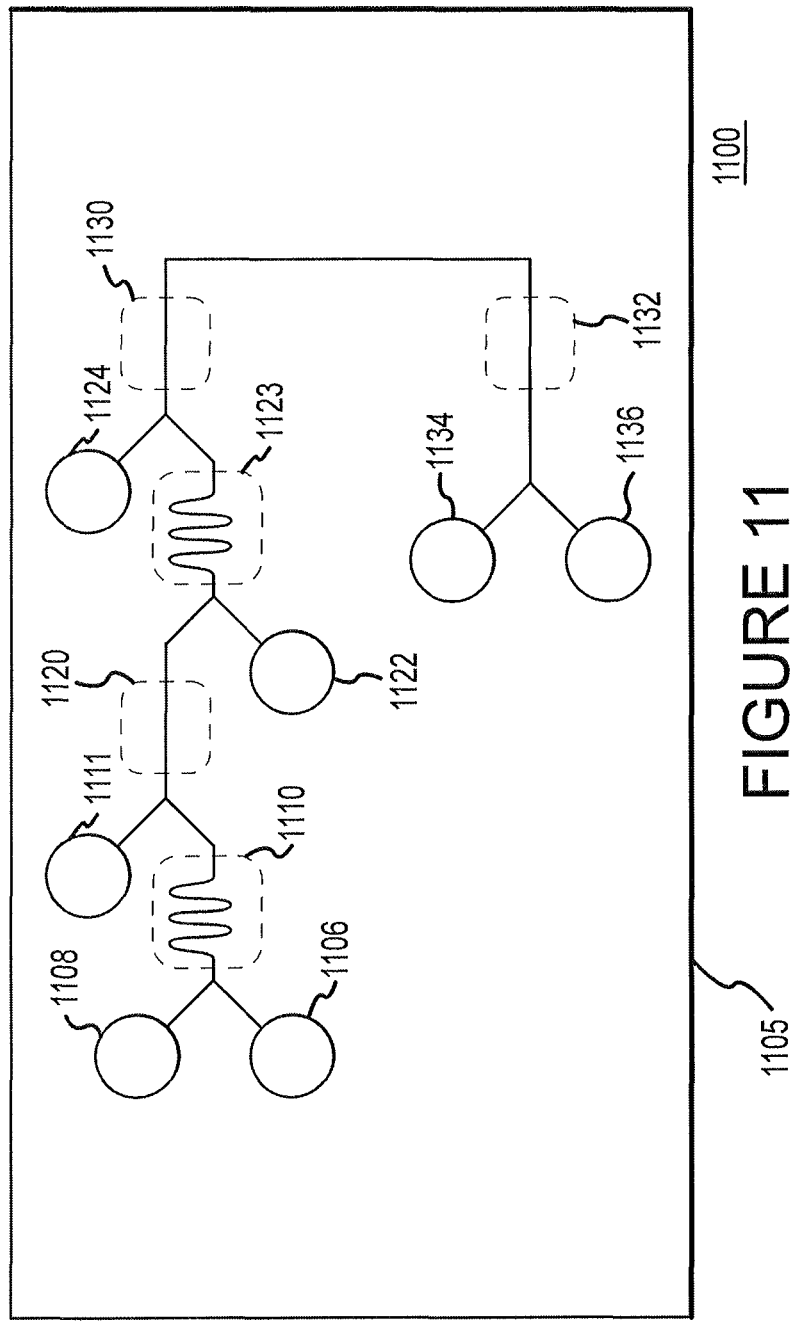
FIG. 11 is a schematic illustration of a top-down view of another microfluidic device arranged in accordance with an embodiment of the present invention.

FIG. 11 is a schematic illustration of a top-down view of another microfluidic device arranged in accordance with an embodiment of the present invention. The microfluidic device 1100 includes a substrate 1105 that may in part define the features shown. An input port 1108 may be provided for input of labels, such as beads. The labels may be magnetic labels, as described above. An input port 1108 may be provided for input of a sample including particles. A region 1110 may be provided in the microfluidic device 1100 for labeling certain particles in the sample received from the input port 1108 with the labels received from the input port 1106. The region 1110 may include, for example, a winding channel as shown to allow for sufficient residence time for labeling, or a chamber, or substantially any other fluidic feature. An input port 1111 may be provided for introduction of a buffer fluid. The buffer fluid and sample including labeled particles may be provided to a separation region 1120 where particles may be separated from the fluid in accordance with examples described above. Another input port 1122 may be provided for introduction of another label, which may be a magnetic label as described above. The label introduced into the input port 1122 may be configured to bind to different particles than those introduced into the input port 1106. Accordingly, different particles may be labeled in the region 1123. Another input port 1124 for a buffer fluid may be provided, and buffer fluid and sample containing labeled particles may be provided to a separation region 1130. An imaging or analysis region 1132 is also provided. In this manner, the microfluidic device 1100 may provide separation of several different particles from a fluid. Optional output ports 1134 and 1136 are also provided.

Microfluidic devices in accordance with embodiments of the present invention may include additional components including but not limited to, pumps, valves, mixers, heaters, coolers, and/or electrodes.

Embodiments of the present invention may include cartridges that are configured to provide microfluidic devices as described herein together with some fluid interfacing components. Some examples of cartridges and cartridge components will now be described.

Figure 12:
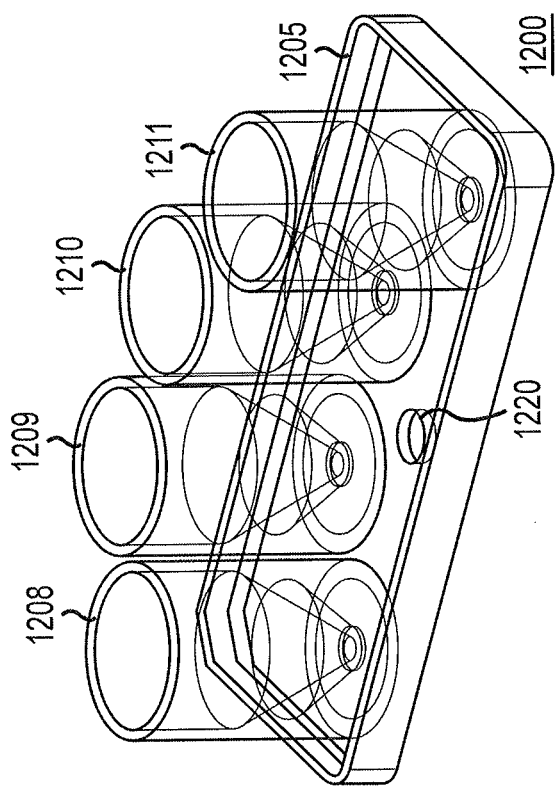
FIG. 12 is a schematic illustration of a portion of a cartridge arranged in accordance with an embodiment of the present invention.

FIG. 12 is a schematic illustration of a portion of a cartridge arranged in accordance with an embodiment of the present invention. The portion of the cartridge shown in FIG. 12 includes a base 1205 and four well structures 1208-1211. The entire structure shown in FIG. 12 may be referred to herein as a well structure insert 1200. The well structure insert may generally be made of any suitable material, including a polymer, and may be formed using molding or embossing techniques, as well as through other methods. Each of the well structures 1208-1211 is configured to contain a fluid and be in fluid communication with an input or output port of a microfluidic device, including any of the input or output ports described above. The well structures 1208-1211 shown in FIG. 12 are shown in a configuration that may be used with the microfluidic device layout shown in FIG. 9, however other inserts are possible that, in an analogous manner, may be used with the other microfluidic devices described herein. Referring to FIG. 12, the well structure 1208 is configured to be in fluid communication with the input port 908 of FIG. 9. The well structure 1209 is configured to be in fluid communication with the input port 910 of FIG. 9. The well structure 1210 is configured to be in fluid communication with the output port 912 of FIG. 9. The well structure 1211 is configured to be in fluid communication with the output port 914 of FIG. 9. It is to be understood that the number and configuration of well structures is quite flexible, and any number or arrangement may be used.

Accordingly, each of the well structures 1208-1211 includes an opening at the bottom of the respective well structure which may provide fluid communication with an input or output port. The microfluidic device, including any inlet or outlet ports, may be provided in the base 1205 itself, or may be bonded or otherwise coupled to the base 1205. For example, the base 1205 may itself form a substrate that defines fluidic features as described herein. In other examples, a separate substrate may be bonded or otherwise coupled to the base 1205.

The well structures 1208-1211 are shown with conically-shaped bottoms. In other examples, the well structures 1208-1211 may have any shape. The conical shaped bottom, however, may be advantageous in some embodiments to lessen or eliminate an amount of fluid or particles in the fluid which does not enter the microfluidic device. For example, referring to FIG. 12, if the well structures 1208-1211 had flat bottoms, particles in fluid contained in one or more of the well structures 1208-1211 may settle in a corner of the well structure and not make it into the fluidic features of the microfluidic device.

The base 1205 also defines an opening 1220 that may be configured to receive a magnet. The magnet may be placed in the opening 1220 during operation, as will be described further below, to perform separation in accordance with the examples described above. In some examples, a removable portion of the microfluidic device, examples of which were described above, may be removed through the opening 1220.

Figure 13:
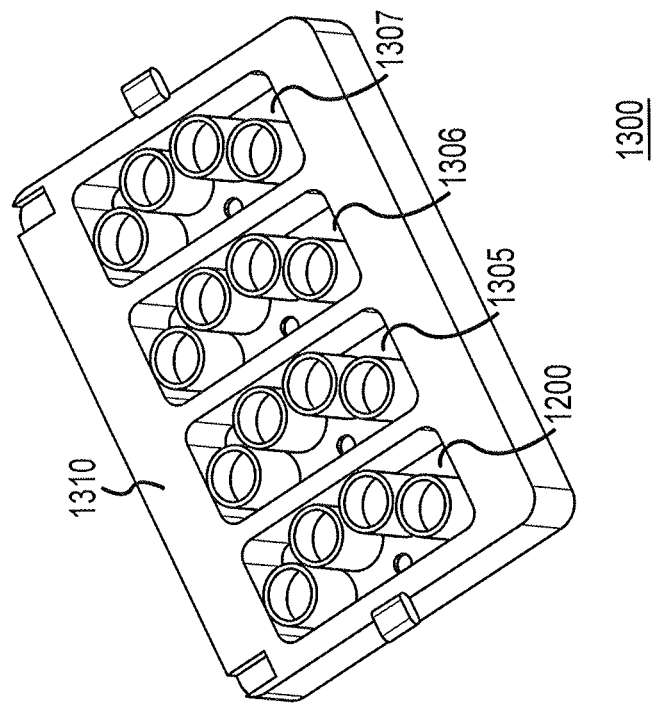
FIG. 13 is a schematic illustration of a cartridge arranged in accordance with an embodiment of the present invention.

FIG. 13 is a schematic illustration of a cartridge arranged in accordance with an embodiment of the present invention. The cartridge 1300 includes four well structure inserts, including the well structure insert 1200 shown in FIG. 12. Three additional well structure inserts 1305-1307 are shown. Any number of well structure inserts may be provided in a cartridge. The well structure insert may include the microfluidic device including fluidic features as described herein, or one or more microfluidic devices may be coupled to the bottom of the respective well structure inserts and/or the cartridge 1300 itself. The well structure inserts 1200 and 1305-1307 are mounted in a frame 1310. The frame 1310 defines four openings sized to receive the four well structure inserts 1200 and 1305-1307. In this manner, the cartridge 1300 may be configured for separation of four separate samples, one in each of the well structure inserts 1200 and 1305-1307. Each of the well structures may be configured to contain a fluid for use during the separation and/or subsequent analysis, examples of which have been described above—including sample, buffer fluid, fluid containing labels, and positive, and negative fractions. A seal may be placed, temporarily or permanently, over the cartridge to contain the fluids within the well structures. This may facilitate efficient transport of the cartridge 1300. In some examples, the well structures may not be completely filled with fluid, but may have an air-fluid interface. A removable pneumatic interface may then be coupled to the cartridge 1300. The removable pneumatic interface may include a gasket forming a pressure seal to one or more of the well structures. The connection to each well structure, or groups of well structures may be addressable. In this manner, automatic control of pressure to each of the well structures may be provided by the pneumatic interface which may provide a pneumatic pressure to one or more selected well structures in parallel, thereby providing fluid flow in the microfluidic devices of the cartridge. This may facilitate automated separation and/or analysis in some examples of the present invention.

A pneumatic interface to the well structures may further allow for use with an instrument that may apply positive or negative pressure to the space above the fluid in each well structure, which does not involve fluid transfer between the instrument and the cartridge. That is, fluid sample, buffer, or positive or negative fractions present in the cartridge may not be flowed into or out of an instrument controlling the separation or analysis conducted on the cartridge in some examples. Such an embodiment may have the advantage of reducing cross-contamination between sequential samples.

FIGS. 14A and 14B are schematic illustrations of a cartridge and a magnet arranged in accordance with an embodiment of the present invention. FIG. 14A illustrates the cartridge 1200 of FIG. 12. The outsides of the well structures 1209-1211 are shown, so the funnel-shaped bottoms of those well structures are obscured in the view of FIG. 14A. A vacuum chuck 1230 which may include a magnet (not visible in FIG. 14A) and attached to a removable substrate 1235 is shown positioned above the opening 1220. As will be described further below, the vacuum chuck 1230 may be lowered into the opening 1220 using pneumatic controls. Other automatic or manual controls may be used in other embodiment. The magnet is not visible in FIG. 14A, it may be an inner magnet inside a housing forming part of the vacuum chuck 1230. The inner magnet 1236 may be circular, fitting into a core of the vacuum chuck, as shown in FIG. 14B. The magnet may be coupled to the removable substrate 1235, which may be used to close off a fluidic feature in a microfluidic device During operation, the vacuum chuck 1230, including the magnet 1236, may be lowered into the opening 1220. In some examples, a removable portion of the microfluidic device is already seated on the microfluidic device, and the vacuum chuck 1230 may then contact the removable portion. In other examples, the vacuum chuck 1230 holds a removable portion of the microfluidic device, and couples the removable portion of the microfluidic device to the microfluidic device when the vacuum chuck 1230 is placed in the opening 1220. That is, pneumatic pressure may hold a removable portion of the microfluidic device (e.g. a substrate) to the vacuum chuck 1230. The pneumatic pressure may be released once the vacuum chuck and removable portion of the microfluidic device are placed through the opening 1220, which may seat the removable portion of the microfluidic device to the microfluidic device. In some examples, the pneumatic pressure is retained to continue to hold the removable portion of the microfluidic device on the vacuum chuck 1230 while the vacuum chuck 1230 and magnet 1236 are placed in the opening 1220, and optionally pressed up against the microfluidic device. Once separation steps have been performed in the microfluidic device, and removal of the removable portion is desired, pneumatic pressure may be applied to hold the removable portion of the microfluidic device against the vacuum chuck 1230, and the magnet and vacuum chuck 1236 and 1230 may be moved up out of the opening 1220 and away from the microfluidic device. The magnet 1236 and vacuum chuck 1230 have been described as coupled together with reference to FIG. 14A, however, in some embodiments the components may be separated. FIG. 14B is a top-down view of the cartridge 1200, showing the magnet 1236 and vacuum chuck positioned in the opening 1220.

Figure 15A:
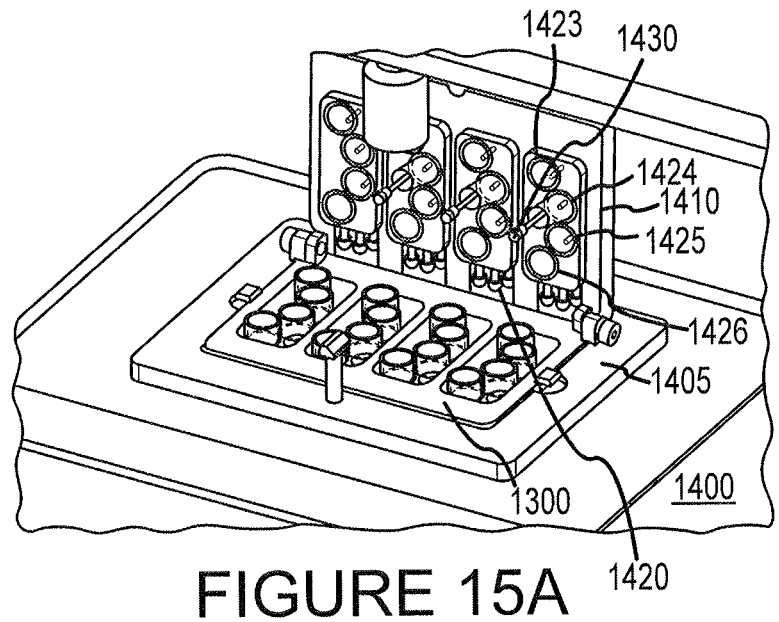
FIGS. 15A and 15B are schematic illustrations of a portion of an instrument arranged in accordance with embodiments of the present invention.
Figure 15B:
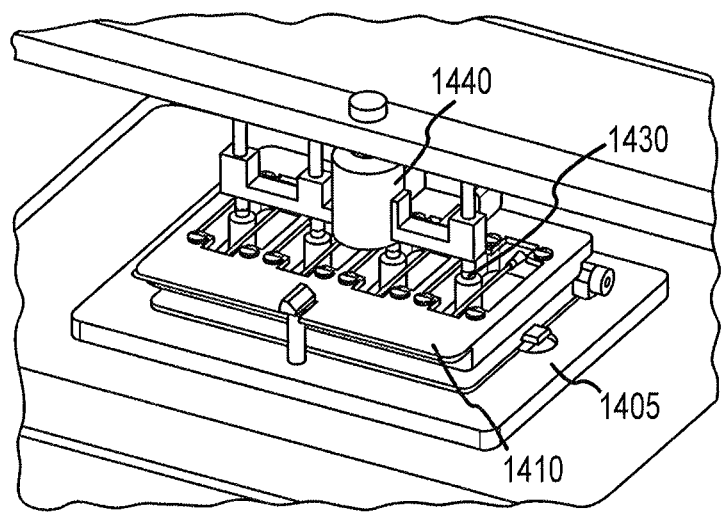

FIGS. 15A and 15B are schematic illustrations of a portion of an instrument arranged in accordance with embodiments of the present invention. The instrument 1400 includes a platform 1405 having an opening configured to receive a cartridge. The cartridge 1300 of FIG. 13, for example, may be inserted into the platform 1405 of the instrument 1400 shown in FIG. 15. The instrument 1400 may further include a cover plate 1410. The cover plate 1410 may include the pneumatic interface for providing pneumatic control of fluid in the well structures, as has generally been described above. Accordingly, as shown in FIG. 15, the cover plate 1410 may include a pneumatic connection to a pressure source (not shown in FIG. 15) provided by the instrument 1400. In FIG. 15, pneumatic connections 1420 are shown that may connect a pressure source to individual regions of the cover plate 1410, which may each correspond to one or more well structures of the cartridge 1300. For example, the regions 1423-1426 are shown in FIG. 15 and may each include a gasket configured to seal a respective one of the well structures of the cartridge 1300 when the cover plate 1410 is in a closed position. Each of the regions 1423-1426 may include a respective pneumatic connection for addressable control of pressure to the well structures. The pneumatic connection may be routed through the material forming the cover plate 1410, or may be provided in an insert to the cover plate 1410 that may match the well structure insert.

The cover plate 1410 further includes a magnet corresponding to each well structure insert of the cartridge 1300. For example, the magnet 1430 is provided corresponding to the first insert as shown in FIG. 15. The magnet 1430 may be coupled to pneumatic controls as well for controlling the position of the magnet. In FIG. 15A, the magnet is shown in an extended position, on a post extending away from the cover plate 1410. The magnet may be retracted by the instrument for control of the magnetic field across portions of the microfluidic device(s) in the cartridge 1300. In addition, the magnet may be retracted along with a removable substrate. The magnet 1230 and vacuum chuck 1235 of FIGS. 14A and 14B may be used to implement the magnet 1430 of FIG. 15, for example.

In FIG. 15B, the cover plate 1410 is shown in a closed position, such that the well structures have been sealed by the cover plate 1410. The magnet assemblies, including magnet assembly 1430 are shown in a retracted position in FIG. 15B. A light source 1440 may also be provided to illuminate the cartridge 1300 for optical analysis.

The pneumatic interface described above may also control the positioning of the magnet. If the microfluidic device used includes a removable portion, the pneumatic interface may further control the introduction of a removable portion, sealing of the removable portion to the microfluidic device, and removal of the removable portion along with any immobilized particles. Removal of the removable portion may be performed by forming a vacuum seal between the removable portion and a vacuum chuck that is movable in the vertical dimension, lifting the vacuum chuck along with the removable portion, moving the cartridge underneath such that the removable portion is above another imaging well having an optically clear bottom, and lowering the removable portion down into the imaging well. Positive pressure may be used to disengage the vacuum chuck and separate it from the removable portion. Another movement of the cartridge can bring the imaging region below a light source if transmittance mode imaging is used. For fluorescent imaging in reflection mode, bottom access to the cartridge may be sufficient and can be done at any time during or after the separation step. In this manner, the instrument may process multiple samples in parallel. Note that the pneumatic interface can multiplex pressure control across a number of wells to drive flow, and across a number of vacuum chucks in order to seal to the removable substrates.

Figure 16:
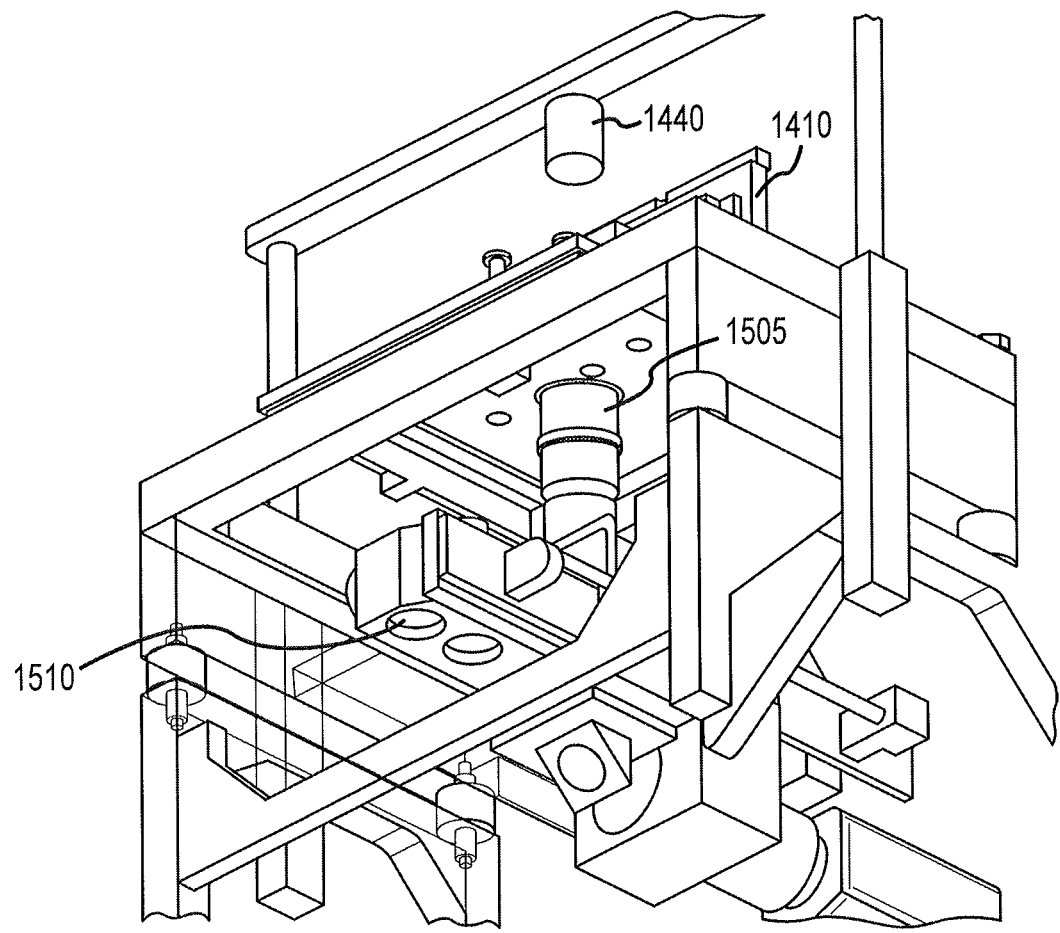
FIG. 16 is a schematic illustration of a portion of an instrument arranged in accordance with embodiments of the present invention.

FIG. 16 is a schematic illustration of a portion of an instrument arranged in accordance with embodiments of the present invention. FIG. 16 shows another view of the instrument 1400 of FIG. 15. The light source 1440 may be seen, as well as a portion of the cover plate 1410. In FIG. 16, an optical objective 1505 is shown which may be positioned beneath the platform for imaging particles within the cartridge. Additional optics, such as a filter cube 1510 may also be provided in the instrument 1400.

In this manner, the instrument may allow for optical access to the underside of the consumable, such as is required in order to image and enumerated the particles. If a removable substrate is used, imaging may be provided by removing the substrate and placing it into another well that has a clear bottom (e.g. cover slip glass).

Although not shown in FIG. 15 or 16, the instrument 1400 may include any number of additional components including, but not limited to, a processing unit (e.g. a CPU and/or a microcontroller), a pressure source, one or more memory devices encoded with executable instructions for execution by the processing unit, additional optical components, heating devices, cooling devices, and/or electronics such as voltage or current sources. The instrument 1400 may include or may be coupled to one or more input or output devices including but not limited to a keyboard, mouse, or display.

Instruments according to examples of the present invention may be configured to provide automated analysis of particles in a fluid. In some examples, the analysis may be automated, however in other examples the analysis may occur partially or completely manually. During operation, a cartridge including a microfluidic device may be placed into the instrument, and one or more pneumatic connections may be made between the instrument and the microfluidic device, such as through examples of the well structures described above. Fluid may be flowed through the microfluidic device to perform any of the separation techniques described above. The fluid flow may be automated in some examples. That is, the instrument may include a processing unit and one or more memory devices encoded with instructions that may cause the processing unit to control the pneumatic interface to apply pressures to the well structures in an order and timing designed to achieve any of the above-described separation mechanisms. The one or more memory device may further be encoded with instructions that may cause the processing unit to control a position of one or magnets and one or more optical objectives.

Accordingly, separation of particles including magnetic labels from a fluid may occur in an automated fashion. The separation may include an automated positioning of a magnet proximate a microfluidic device. In some examples, imaging of the particles may occur, and the imaging may occur through an automated positioning of an optical objective proximate the microfluidic device. As has been described above, in some examples, a portion of the microfluidic device may be removed. The memory device included in examples of instruments described herein may further include instructions for causing a processor to control a pneumatic arm or other structure to remove the removable portion of the microfluidic device. The instructions may further cause the removable portion of the microfluidic device to be placed in a different location for subsequent analysis.

Embodiments of methods, microfluidic devices, and instruments have accordingly been described above that may be used for magnetic separation. In one example, cells may be separated using above-described techniques from a sample having a very low concentration (e.g. 1-500 cells/$1 \times 10^6$ cells). Magnetic beads may be bound to circulating tumor cells in patient blood samples that may have a similar order of concentration, and may be detectably separated from leukocytes and red blood cells, the negative fraction cells.

Embodiments described above may achieve advantages over presently available systems for magnetic separation. Some advantages will now be described, although the advantages are not to be used to limit the scope of any claims or embodiments described herein. It is to be understood that not all embodiments will achieve all the described advantages, and some embodiments may not achieve any of the stated advantages.

1. Higher capture efficiency and purity. Because delivery of the sample to a separation region may be performed via microfluidics, cells may pass closer to the magnetic source (for example within 50 uM in some embodiments, or 100 um in some embodiments, or 1-5 mm in some embodiments), therefore higher field gradients may be applied to the sample, leading to higher capture efficiency and positive fraction purity as compared to other approaches. Since the separation region may have a lower flow velocity and lower shear with respect to the rest of the flow channel, smaller magnetic forces may be used to separate cells for a given level of magnetic susceptibility of the positive fraction. Because multiple divergent forces may be applied to the sample (e.g. magnetic forces and gravitational forces) the purity may be enhanced as the secondary force aids in driving the negative fraction to a 'waste' outlet.

2. Reduced sample loss. Described embodiments include a number of features that may reduce sample loss ahead of the sample reaching the separation region. First, described well structures may include a conical-shaped bottom, which may reduce the effect of settling. For a simple rectangular well, a large number of particles in a sample may settle on the bottom, around the microfluidic inlet port. In other examples described herein, the geometry used may permit short run times for the given sample volumes (e.g. 0.5-10 mL), so there may be a shorter time during which the sample cells can aggregated and/or settle in the inlet chamber and the microfluidic device. Furthermore, the same starting sample may be run through a number of parallel microfluidic channels/separation chambers, further reducing run time and loss by settling, aggregation or loss of cell viability.

3. Higher recovery percentage. Some described embodiments include a removable substrate on which the target particles (positive fraction) may be immobilized. This may be advantageous for achieving higher recovery of target cells into an analysis vessel (or final analysis volume). That is because an elution step may not be required, whereby the magnetic field is removed or the cells are lysed and driven via flow from a separation region and into an analysis region, which can result in poor efficiency and dilute samples. Another advantage of the removable substrate is that the analysis volume can be very small, and may not be required to be larger than the separation region volume and/or the wash volume; this may be the case for techniques where flow is used but no removable substrate is present.

4. Better analysis of the captured cells, and improved identification of target cells. For circulating tumor cells, for example, it may be beneficial to be able to determine the nature off the captured cells, purity and other parameters via imaging under a microscope. Embodiments described above include the ability to image the cells being captured either during the capture step, or post capture if a removable substrate is used and positioned in a second chamber where the cells are in a planar configuration and positioned in the proximity of a high powered microscope objective, on top of a high optical quality substrate such as coverslip glass. Other systems don't offer the ability to analyze the sample during separation, or image it with high resolution after the separation step.

5. Automation capability. The capability for system automation may be improved by using a cartridge that includes examples of the described well structures, which may be compatible with standard liquid handing equipment and equipment capable of moving the cartridge from one location to another inside the instrument. Furthermore, automation may be improved by the capability of running multiple separation experiments in parallel using a simple interface.

6. Capability for highly accurate genetic and proteomic analysis. Often, the accuracy of genetic (e.g. DNA, RNA) or proteomic analysis of a cell sample may be determined by the ability of separating the cells/cellular material of interest into a small analysis volume and at a high purity. Both aims may be achieved by examples described above through the use of a number of improved features, including the use of a removable substrate. The removable substrate has the positive fraction cells attached, and may be washed before the cells are resuspended or lysed in very small volumes, ranging from a few nL, to a few uL to a fraction of a mL. Washing may be enhanced because target cells are magnetized and will remain attached, leading to better purity. Because cells are attached to a substrate, they can be simply resuspended into a secondary container without bringing along any of the non-target cells that aren't bound to the substrate, but may be present in the rest of the separation chamber. This may lead to improved purity and improved genetic and proteomic analysis.

7. The ability to capture and analyze individual cells. Microfluidic designs described above may be used for the sequestration and analysis of single cells from either the positive or negative cell fraction.

From the foregoing it will be appreciated that, although specific embodiments of the invention have been described herein for purposes of illustration, various modifications may be made without deviating from the spirit and scope of the invention.

What is claimed is:

1. A method comprising:
providing a fluid containing a plurality of particles having magnetic labels in a microfluidic device, wherein the microfluidic device includes:
a first substrate at least partially defining a fluidic feature having an opening;
a second substrate reversibly forming a portion of the fluidic feature by covering the opening;
separating the plurality of particles having magnetic labels from the fluid during flow of the fluid in the microfluidic device at least in part by generating a magnetic field across the microfluidic device such that the plurality of particles having magnetic labels are transferred to the second substrate; and
removing the second substrate including the plurality of particles having magnetic labels from the opening.

2. The method of claim 1, wherein said separating the plurality of particles having magnetic labels from the fluid sample comprises positioning a magnet proximate the microfluidic device.

3. The method of claim 2, further comprising:
placing the microfluidic device into an analysis instrument including a magnet coupled to a pneumatic interface; and
wherein said positioning a magnet proximate the microfluidic device comprises pneumatically deploying magnet through the pneumatic interface.

4. The method of claim 1, wherein said generating a magnetic field across the microfluidic device comprises generating a force on the plurality of particles having magnetic labels in a direction opposite to a gravitational force.

5. The method of claim 4, wherein said separating the plurality of particles having magnetic labels comprises sedimenting another plurality of particles substantially free from magnetic labels.

6. The method of claim 5, wherein said another plurality of particles include labels configured to increase the sedimentation velocity of the another plurality of particles.

7. The method of claim 1, further comprising generating an image of the particles having magnetic labels on the second substrate.

8. The method of claim 1, wherein the fluidic feature is a first fluidic feature, and wherein said introducing a fluid containing a plurality of particles having magnetic labels into a microfluidic device comprises introducing the fluid into a second fluidic feature of the microfluidic device, wherein the first and second fluidic features are in fluid communication, and wherein a cross-sectional dimension of the first fluidic feature is larger than a cross-section dimension of the second fluidic feature such that particles experience reduced flow velocity during flow in the first fluidic feature relative to the second fluidic feature.

9. The method of claim 1, wherein introducing a fluid sample containing a plurality of particles having magnetic labels into a microfluidic device comprises flowing the fluid sample into the fluidic feature in a first stream, wherein the method further comprises:

flowing another fluid into the fluidic feature in a second stream, and wherein the magnet is positioned such that the plurality of particles having magnetic labels in the first stream are transported across the second stream at least in part by the magnetic field.

10. The method of claim 1, further comprising analyzing the particles including magnetic labels, wherein said analyzing comprises cell biomarker analysis.

11. The method of claim 10, wherein said cell biomarker analysis includes genetic, RNA, protein-based, metabolic, or signaling biomarkers, or combinations thereof.

12. The method of claim 1, further comprising analyzing of one or more of the particles including magnetic labels using PCR, FISH, sequencing, RNA analysis, protein analysis, signaling analysis, phosphorylation state analysis, or combinations thereof.

13. The method of claim 1, wherein said particles comprise cells and wherein the method further comprises culturing the cells after separation.

14. The method of claim 1, further comprising, after removing said second substrate, coupling the second substrate to a vessel.

15. The method of claim 1, wherein the second substrate reversibly seals to and closes the opening.

16. The method of claim 15, further comprising flowing the fluid in the fluidic feature, past the opening.

17. The method of claim 1, wherein the opening is in a wall of the fluidic feature such that the fluid flows past the opening when flowing through the fluidic feature.

18. The method of claim 1, wherein the fluidic feature is a channel and wherein the second substrate defines a portion of the channel when positioned to seal the opening.

19. The method of claim 1, further comprising inserting at least a portion of the second substrate into the fluidic feature.

20. The method of claim 1, wherein one or more particles of the plurality of particles having magnetic labels are tumor cells.

21. The method of claim 1, wherein the second substrate include one or more well structures.

22. The method of claim 21, wherein the one or more well structures comprise multiple well structures connected together by a base.

23. The method of claim 22, wherein the multiple well structures each include an opening at the bottom of the respective well structure.

24. The method of claim 23, wherein the multiple well structures each include a conically-shaped bottom.

* * * * *